United States Patent
Chapman et al.

(10) Patent No.: US 6,518,273 B1
(45) Date of Patent: Feb. 11, 2003

(54) 2-ARYL INDOLE DERIVATIVE AS ANTAGONISTS OF TACHYKININS

(75) Inventors: Kevin Tyler Chapman, Scotch Plains, NJ (US); Kevin Dinnell, Harlow (GB); Jason Matthew Elliott, Harlow (GB); Gregory John Hollingworth, Harlow (GB); Steven Michael Hutchins, Hillsborough, NJ (US); Duncan Edward Shaw, Harlow (GB); Christopher Alan Willoughby, Green Brook, NJ (US)

(73) Assignee: Merck Sharp & Dohme Ltd., Hoddesdon (*) Notice: Subject to any disclaimer, the term of this patent is extended or adjusted under 35 U.S.C. 154(b) by 0 days.

(21) Appl. No.: 09/914,893

(22) PCT Filed: Feb. 23, 2000

(86) PCT No.: PCT/GB00/00650
§ 371 (c)(1), (2), (4) Date: Sep. 4, 2001

(87) PCT Pub. No.: WO00/51984
PCT Pub. Date: Sep. 8, 2000

(30) Foreign Application Priority Data

Mar. 4, 1999 (GB) .............................................. 9905010

(51) Int. Cl.[7] .................... A61K 31/496; C07D 403/06; C07D 487/08
(52) U.S. Cl. ............................ 514/253.05; 514/254.09; 514/414; 514/241; 514/242; 514/252.02; 514/252.19; 514/253.09; 514/254.02; 514/254.03; 514/254.04; 514/254.05; 544/363; 544/373; 544/180; 544/182; 544/238; 544/295; 544/357; 544/364; 544/366; 544/367; 544/369; 544/370; 548/453
(58) Field of Search .................................. 544/373, 363; 514/254.09, 414, 253.05; 548/453

(56) References Cited

U.S. PATENT DOCUMENTS 3,242,192 A * 3/1966 Shen et al. .................. 544/373

FOREIGN PATENT DOCUMENTS

| EP | 0 655 442 | 5/1995 |
| GB | 2 311 523 | 10/1997 |

OTHER PUBLICATIONS

Ohnmacht et al. in Annual Reports in Medicinal Chemistry, vol. 33,pp. 71–80 (1998).*

* cited by examiner

*Primary Examiner*—Emily Bernhardt
(74) *Attorney, Agent, or Firm*—J. Eric Thies; Melvin Winokur

(57) ABSTRACT

The present invention relates to compounds of the formula (I):

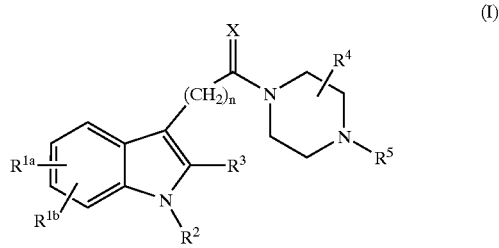

wherein $R^{1a}, R^{1b}, R^2, R^3, R^4, R^5$, X and n are defined herein. The compounds are of particular use in the treatment or prevention of depression, anxiety, pain, inflammation, migraine, emesis and postherpetic neuralgia.

6 Claims, No Drawings

2-ARYL INDOLE DERIVATIVE AS ANTAGONISTS OF TACHYKININS

CROSS REFERENCE TO RELATED APPLICATIONS

This application is a U.S. National Phase application under 35 U.S.C. §371 of PCT Application No. PCT/GB00/00650, filed Feb. 23, 2000, which claims priority under 35 U.S.C. §119 from GB Application No. 9905010.6, filed Mar. 4, 1999.

This invention relates to indole derivatives and their use as tachykinin antagonists, and in particular as neurokinin-1 receptor antagonists.

We have now found a class of indole derivatives which are potent receptor antagonists of tachykinins, especially of the neurokinin-1 (substance P) receptor.

The present invention accordingly provides the compounds of the formula (I):

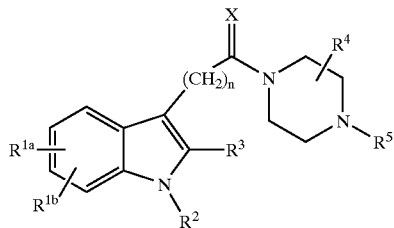

wherein
- $R^{1a}$ and $R^{1b}$ each independently represent hydrogen, $C_{1-6}$alkyl, $C_{1-6}$alkoxy, fluoro$C_{1-6}$alkyl, fluoro$C_{1-6}$alkoxy, halogen, cyano, $NR^aR^b$, $SR^a$, $SOR^a$, $SO_2R^a$, $OSO_2R^a$, $NR^aCOR^b$, $COR^a$, $CO_2R^a$ or $CONR^aR^b$;
- $R^2$ represents hydrogen, $C_{1-6}$alkyl, fluoro$C_{1-6}$alkyl, $(CH_2)_mCOR^a$, $(CH_2)_pCO_2R^a$, $(CH_2)_pOH$, $(CH_2)_mCONR^aR^b$, $(CH_2)_m$phenyl or $SO_2C_{1-6}$alkyl;
- $R^3$ represents phenyl, biphenyl or naphthyl, wherein said phenyl, biphenyl or naphthyl group may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl or $C_{1-4}$alkoxy$C_{1-4}$alkyl;
- $R^4$ represents hydrogen, $C_{1-6}$alkyl, carbonyl (=O), $(CH_2)_p$phenyl or a $C_{1-2}$alkylene bridge across the piperazine ring;
- $R^5$ represents $C_{1-6}$alkyl, $C_{3-7}$cycloalkyl, $C_{3-7}$cycloalkyl$C_{1-4}$alkyl, $C_{2-6}$alkenyl, phenyl, naphthyl, fluorenyl, heteroaryl, $(CH_2)_p$phenyl, $(CH_2)_p$heteroaryl, $CH(phenyl)_2$, $CH(C_{1-6}alkyl)$ (phenyl), $C_{2-4}$alkenyl(phenyl), $(CH_2)_pNR^cR^d$, $(CH_2)_pCONR^cR^d$, $(CH_2)_mCOR^c$, $(CH_2)_mCO_2R^c$ or $(CH_2)_pOH$;
- $R^a$ and $R^b$ each independently represent hydrogen, $C_{1-4}$alkyl or fluoro$C_{1-4}$alkyl;
- $R^c$ and $R^d$ each independently represent hydrogen, $C_{1-4}$alkyl, fluoro$C_{1-4}$alkyl, $C_{2-4}$alkenyl, phenyl or benzyl or $R^c$ and $R^d$, together with the nitrogen atom to which they are attached, form a heteroaliphatic ring of 4 to 7 atoms, to which ring there may optionally be fused a benzene ring, and wherein said phenyl, naphthyl, fluorenyl or heteroaryl groups may be optionally substituted by one, two or three groups independently selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$, $SOR^a$, $SO_2R^a$, $COR^a$, $CO_2R^a$, $CONR^aR^b$, $C_{2-6}$alkenyl, $C_{2-6}$alkynyl, $C_{1-4}$alkoxy$C_{1-4}$alkyl or —O$(CH_2)_{1-2}$O—;
- X represents an oxygen or a sulfur atom;
- m is zero or an integer from 1 to 4;
- n is an integer from 1 to 4;
- p is an integer from 1 to 4;

or a pharmaceutically acceptable salt thereof.

A preferred group of compounds of formula (I) is that wherein $R^{1a}$ and $R^{1b}$ each independently represent hydrogen, $C_{1-6}$aLkyl, fluoro$C_{1-6}$alkoxy or halogen. Where $R^{1a}$ and $R^{1b}$ are both other than hydrogen, preferably $R^{1a}$ and $R^{1b}$ are the same. Where $R^{1a}$ is other than hydrogen and $R^{1b}$ is hydrogen, $R^{1a}$ is preferably attached to the indole ring at the 5-position.

A particularly preferred group of compounds of formula (I) is that wherein $R^{1a}$ and $R^{1b}$ each independently represent hydrogen, methyl, trifluoromethoxy, fluorine or chlorine.

As especially preferred group of compounds of formula (I) is that wherein $R^{1a}$ represents 5-methyl or 5-chloro, and $R^{1b}$ is hydrogen.

A further preferred group of compounds of formula (I) is that wherein $R^2$ represents hydrogen, $C_{1-6}$alkyl, fluoro$C_{1-6}$alkyl, $(CH_2)_mCOR^a$, $(CH_2)_pCOR^a$, $(CH_2)_pOH$ or $(CH_2)_m$phenyl.

A particularly preferred group of compounds of formula (I) is that wherein $R^2$ represents $C_{1-3}$alkyl (especially methyl, ethyl or isopropyl), fluoro$C_{1-3}$alkyl (especially trifluoromethyl or 2,2,2-trifluoroethyl), $COCH_3$, $CH_2CO_2H$, $CH_2CO_2CH_3$, $(CH_2)_{1-2}OH$ (especially $CH_2CH_2OH$) or benzyl.

An especially preferred group of compounds of formula (I) is that wherein $R^2$ is hydrogen or methyl.

Another preferred group of compounds of formula (I) is that wherein $R^3$ represents phenyl, biphenyl or naphthyl (especially 2-naphthyl) wherein said phenyl group is optionally substituted by one or two groups selected from halogen, $C_{1-6}$alkyl, $C_{1-6}$alkoxy, trifluoro$C_{1-6}$alkyl, fluoro$C_{1-6}$alkoxy or $C_{2-6}$alkenyl.

A particularly preferred class of compounds of formula (I) is that wherein $R^3$ represents phenyl, biphenyl or naphthyl (especially 2-naphthyl) wherein said phenyl group is optionally substituted by one or two groups selected from chlorine, bromine, $C_{1-4}$alkyl (especially isopropyl or tertiary butyl), methoxy, trifluoromethyl, trifluoromethoxy or vinyl.

An especially preferred group of compounds of formula (I) is that wherein $R^3$ represents phenyl optionally substituted by one or two groups selected from chlorine, bromine, $C_{1-4}$alkyl (especially isopropyl or tertiary butyl), methoxy, trifluoromethyl, trifluoromethoxy or vinyl.

A further preferred group of compounds of formula (I) is that wherein $R^4$ represents hydrogen, methyl, carbonyl, benzyl or a methylene bridge across the 2,5-positions on the piperazine ring.

As especially preferred group of compounds of formula (I) is that wherein $R^4$ is hydrogen.

Another preferred group of compounds of formula (I) is that wherein $R^5$ represents $C_{1-6}$alkyl, $C_{3-7}$cycloalkyl, $C_{3-7}$cycloalkyl$C_{1-4}$alkyl, $C_{2-6}$alkenyl, phenyl, naphthyl, fluorenyl, heteroaryl, $(CH_2)_p$phenyl, $(CH_2)_p$heteroaryl, $CH(phenyl)_2$, $CH(C_{1-6}alkyl)(phenyl)$, $C_{2-4}$alkenyl(phenyl), $(CH_2)_pNR^cR^d$, $(CH_2)_pCONRCR^d$, $(CH_2)_mCOR^c$ or $(CH_2)_mCO_2R^c$ wherein said phenyl or heteroaryl group is optionally substituted by one or two substituents selected from halogen, $C_{1-6}$alkyl, $C_{1-6}$alkoxy, fluoro$C_{1-6}$alkyl, fluoro$C_{1-6}$alkoxy, $NO_2$, cyano, $SR^a$ or —O$(CH_2)_{1-2}$O—.

A particularly preferred group of compounds of formula (I) is that wherein $R^5$ represents $C_{3-6}$alkyl (especially propyl, isopropyl or isopentyl), $C_{5-7}$cycloalkyl (especially cyclohexyl), $C_{3-7}$cycloalkyl$C_{1-2}$alkyl (especially cyclopropylmethyl, cyclohexylmethyl or 2-cyclohexylethyl), $C_{2-4}$alkenyl (especially vinyl), phenyl, naphthyl (especially 1-naphthyl), fluorenyl (especially 9-fluorenyl), heteroaryl, $(CH_2)_p$phenyl (especially wherein p is 1 or 2), $(CH_2)_p$heteroaryl (especially wherein p is 1), CH(phenyl)$_2$, CH($C_{1-2}$alkyl)(phenyl), $C_{2-4}$alkenyl(phenyl) (especially CH$_2$—CH=CHphenyl), $(CH_2)_p$NR$^c$R$^d$ (especially where R$^c$ and R$^d$ each represent $C_{2-4}$alkenyl; and especially wherein p is 2), $(CH_2)_p$CONR$^c$R$^d$ (especially wherein R$^c$ and R$^d$ each independently represent hydrogen, $C_{1-4}$alkyl, $C_{2-4}$alkenyl, phenyl or benzyl or R$^c$ and R$^d$, together with the nitrogen atom to which they are attached, form a heteroaliphatic ring of 5 or 6 atoms to which ring there is fused a benzene ring; and especially wherein p is 1), $(CH_2)_m$COR$^c$ (especially wherein R$^c$ represents phenyl; and especially wherein m is zero) or $(CH_2)_m$CO$_2$R$^c$ (especially wherein R$^c$ represents hydrogen or $C_{1-4}$alkyl; and especially wherein m is zero or 1), wherein said phenyl or heteroaryl groups may be substituted by one or two groups independently selected from halogen, $C_{1-4}$alkyl, $C_{1-4}$alkoxy, fluoro$C_{1-4}$alkyl, fluoro$C_{1-4}$alkoxy, NO$_2$, cyano and SR$^a$ (especially wherein R$^a$ represents $C_{1-4}$alkyl), or said phenyl or heteroaryl group may be substituted by the group —O(CH$_2$)$_{1-2}$O—. Particularly preferred are compounds in which said phenyl groups are unsubstituted or substituted by one or two substituents independently selected from fluorine, chlorine, methyl, ethyl, methoxy, ethoxy, isopropoxy, trifluoromethoxy, nitro, cyano and thiomethyl, or said phenyl is substituted by —OCH$_2$O—. Also preferred are compounds in which said heteroaryl groups are unsubstituted or are monosubstituted by methyl or trifluoromethyl.

Another preferred group of compounds of formula (I) is that wherein X represents an oxygen atom.

A further preferred group of compounds of formula (I) is that wherein n is 2, 3 or 4, and especially wherein n is 2.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hydrogen atoms have been replaced by fluorine atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Examples of such groups include pyrrolyl, furanyl, thienyl pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl. Particularly preferred examples of "heteroaryl" groups include pyridyl and triazolyl, especially 2-pyridyl and 1,2,4-triazol-3-yl.

When used herein the term "halogen" means fluorine, chlorine, bromine and iodine. The most apt halogens are fluorine and chlorine of which fluorine is preferred, unless otherwise stated.

A particularly preferred compound of the present invention is the compound of formula (Ia)

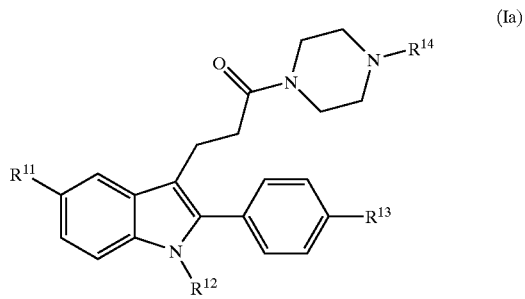

(Ia)

or a pharmaceutically acceptable salt thereof wherein
$R^{11}$ represents a chlorine atom or a methyl group;
$R^{12}$ represents a hydrogen atom or a group selected from $C_{1-3}$alkyl, fluoro$C_{1-3}$alkyl, COCH$_3$, or (CH$_2$)$_2$OH;
$R^{13}$ represents a halogen atom or a group selected from $C_{1-4}$alkyl, $C_{2-4}$alkenyl, fluoro$C_{1-4}$alkyl, $C_{1-4}$alkoxy or fluoro$C_{1-4}$alkoxy; and
$R^{14}$ represents a group selected from $C_{3-6}$alkyl, $C_{5-7}$cycloalkyl, $C_{3-7}$cycloalkyl$C_{1-2}$alkyl, phenyl, naphthyl, benzyl, α-methylbenzyl, phenylethyl, —CH$_2$CON(CH$_3$)phenyl, —CH$_2$CON(CH$_3$)benzyl, —CH$_2$CONR$^c$R$^d$ (where R$^c$ and R$^d$, together with the nitrogen atom to which they are attached, form a heteroaliphatic ring of 5 or 6 atoms to which ring there is fused a benzene ring), —CH$_2$CON(CH$_3$)C$_{2-4}$alkenyl, or —(CH$_2$)$_m$CO$_2$R$^c$ (where R$^c$ is hydrogen or C$_{1-4}$alkyl and m is zero or 1), wherein said phenyl and benzyl groups may be substituted by a group selected from halogen, $C_{1-3}$alkyl, $C_{1-3}$alkoxy, fluoro$C_{1-3}$alkyl, fluoro$C_{1-3}$alkoxy, NO$_2$, cyano, and —S—$C_{1-3}$alkyl or said phenyl and benzyl groups may be substituted by the group —O—CH$_2$—O—.

Particularly preferred compounds of formula (Ia) are those wherein $R^{12}$ represents hydrogen, methyl, COCH$_3$ or —(CH$_2$)$_2$OH, especially hydrogen or methyl.

Another preferred class of compounds of formula (Ia) is that wherein $R^{13}$ represents chlorine, bromine, methyl, ethyl, isopropyl, trifluoromethyl or vinyl, especially chlorine or bromine.

A further preferred class of compounds of formula (Ia) is that wherein $R^{14}$ represents phenyl, benzyl, cyclohexyl, cyclohexylmethyl, cyclopropylmethyl, isopentyl, —CH$_2$CON(CH$_3$)phenyl, —CH$_2$CON(CH$_3$)benzyl, or —CH$_2$CO$_2$CH$_2$CH$_3$, wherein said phenyl and benzyl groups may be substituted by a group selected from fluorine, chlorine, methyl, methoxy, trifluoromethoxy, NO$_2$, methylthio or by the group —O—CH$_2$—O—.

An especially preferred class of compound of formula (Ia) is that wherein $R^{14}$ represents 2-methoxyphenyl.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula (I) and salts thereof, for example, hydrates.

The compounds according to the invention may have at least one asymmetric centre, and may exist both as enantiomers and as diastereoisomers. It is to be understood that all such isomers and mixtures thereof are encompassed within the scope of the present invention.

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, wafers, powders, granules, solutions or suspensions, or suppositories, for oral, parenteral or rectal administration, or administration by inhalation or insufflation. Oral compositions such as tablets, pills, capsules or wafers, are particularly preferred.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, bronchospasm and cough; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-$HT_3$ antagonist, such as ondansetron, granisetron or tropisetron, or other anti-emetic medicaments, for example, a dopamine antagonist such as metoclopramide or domperidone or $GABA_B$ receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

Suitable methods for determining the anti-emetic effects of compounds of the present invention are well known in the art, for example, using the ferret model of cisplatin-induced emesis described by F. D. Tattersall et al, in *Eur. J. Pharmacol.*, (1993) 250, R5–R6.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or depression.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5\text{-}HT_{1A}$ agonists or antagonists, especially $5\text{-}HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-}HT_{1A}$ receptor agonists or antagonists include, in particular, the $5\text{-}HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders, including obesity, bulimia nervosa and compulsive eating disorders.

The present invention also provides a method for the treatment or prevention of eating disorders, including obesity, bulimia nervosa and compulsive eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m$^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma. the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

Several methods for preparing the compounds of the present invention are illustrated in the following schemes and Examples wherein $R^1$, $R^2$, $R^3$, $R^4$, $R^5$, X and n are as defined above unless otherwise specified.

Abbreviations Used in the Schemes

Reagents

AcCl acetyl chloride
AcOH acetic acid
$BH_3$.THF borane-tetrahydrofuran complex
$BrCH_2CN$ bromoacetonitrile
$C_6F_5CH_2OH$ pentafluorobenzyl alcohol
CDI carbonyldiimidazole
DIAD diisopropyl azodicarboxylate
DIBAL-H diisobutylaluminium hydride
DIC 2-dimethylaminoisopropyl chloride hydrochloride
DMAP 4-dimethylaminopyridine
DMSO dimethylsulfoxide
(DPPB)PdCl$_2$ [1,4-butanediylbis(diphenylphosphine)]dichloropalladium
EDC 1-(3-dimethylaminopropyl)-3-ethylcarbodiimide hydrochloride
Et$_3$N triethylamine
EtOH ethanol
H$_2$, Pd-C catalytic hydrogenation using palladium on carbon
HCl hydrochloric acid
HOBT 1-hydroxybenzotriazole hydrate
iPr$_2$EtN diisopropylethylamine
K$_2$CO$_3$ potassium carbonate
KOt-Bu potassium tert-butoxide
MeOH methanol
Na(AcO)$_3$BH sodium triacetoxyborohydride
NaH sodium hydride
NaOH sodium hydroxide
Pd$_2$(DBA)$_3$ tris(dibenzylideneacetone)dipalladium (0)
Ph$_3$P triphenylphosphine
(RS)-BINAP (R,S)-2,2'-bis(diphenylphosphino)-1,1'-binaphthyl
TFA trifluoroacetic acid
TMSBr bromotrimethylsilane
ZnCl$_2$ zinc chloride

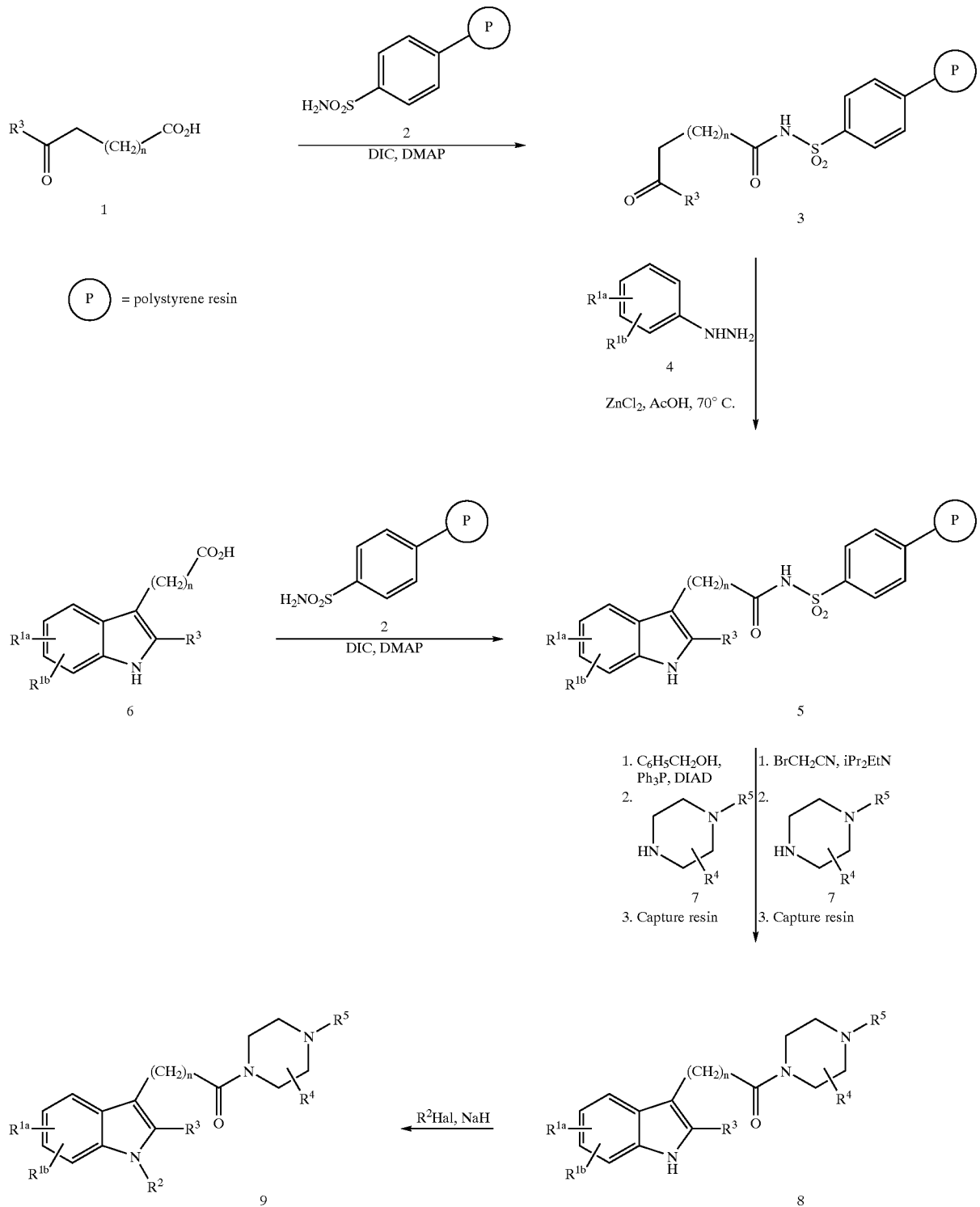

Scheme 2
Synthesis of acid 6 where n = 1

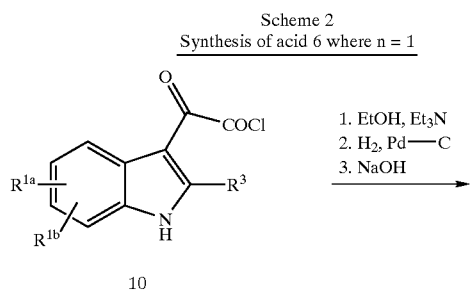

Scheme 3
Synthesis of acid 6 where n = 2

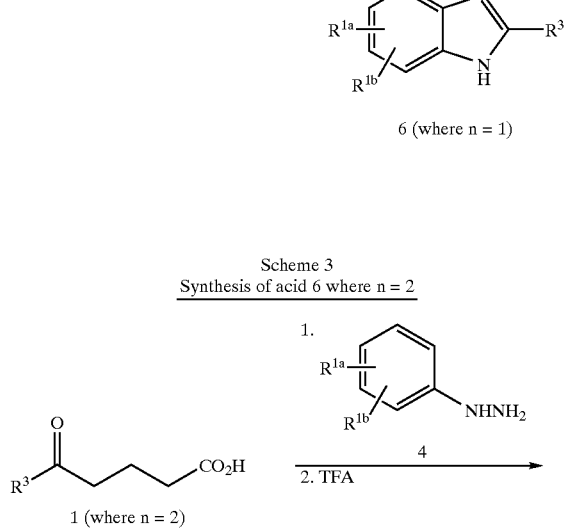

Scheme 4
Synthesis of amines 7 (where R⁵ is substituted phenyl)

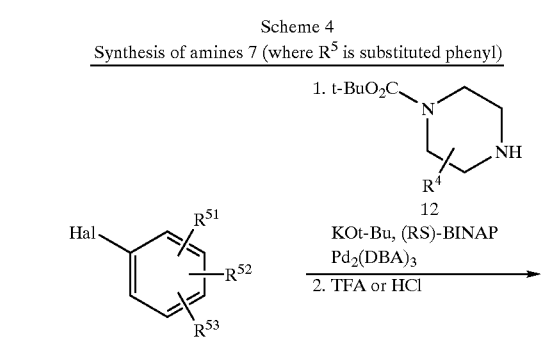

where R⁵¹, R⁵² and R⁵³ represent one, two or three optional substituents as defined in formula (I) and Hal is a leaving group such as bromide or iodine

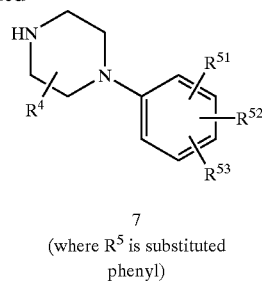

7
(where R⁵ is substituted phenyl)

Scheme 5
Coupling reaction (where X = O)

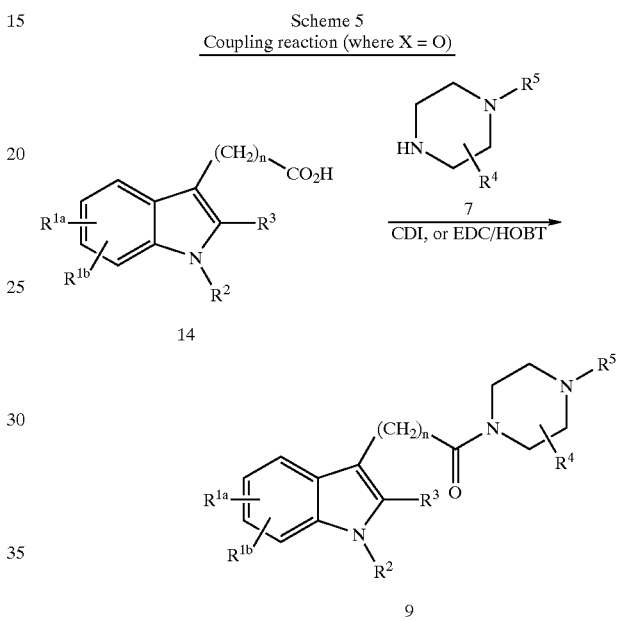

Scheme 6
Coupling reaction (addition of R³) (where X = O)

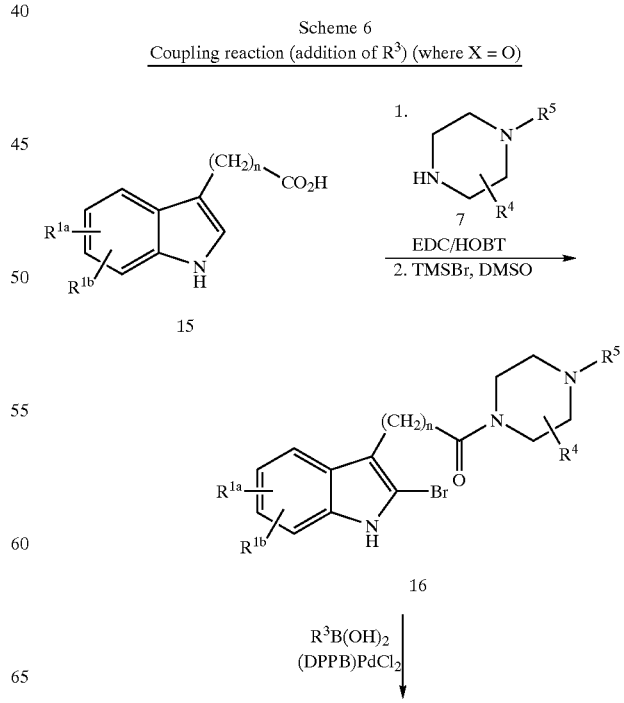

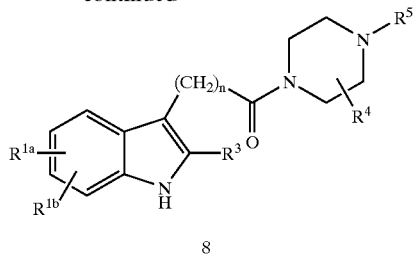

Scheme 7
Coupling reaction (addition of R⁵) (where X = O)

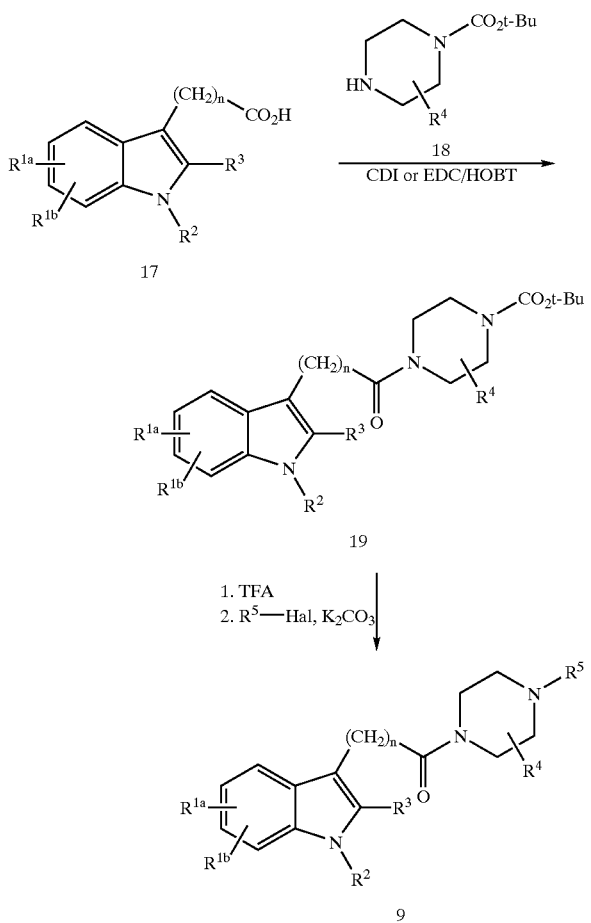

The compounds of the present invention in which X=O may be prepared by the general route outlined in Scheme 1 or by methods analogous thereto. Thus, the appropriate carboxylic acid 1 is loaded onto a resin 2, for example, 4-sulfamylbutyryl AM resin (Novabiochem), using a suitable coupling agent such as 1,3-diisopropylcarbodiimide. The reaction is conveniently effected in the presence of an organic base such as 4-dimethylaminopyridine. The resultant loaded resin 3 may then be reacted with phenyl hydrazine or with a variety of mono- or disubstituted phenyl hydrazines 4 to prepare the indole intermediate 5 which, at this stage, is still bound to the resin. Reaction with the hydrazine is an example of the well-known Fischer indole synthesis, conveniently effected in glacial acetic acid in the presence of a suitable catalyst, for example, a Lewis acid such as zinc chloride.

An alternative route to the resin bound indoles 5 involves the coupling of a preformed indole carboxylic acid 6 with the resin 2 using the conditions described above.

Preparation of the compounds of formula (I) is completed by an exchange reaction that liberates the resin and introduces the substituted piperazine moiety. This exchange reaction may be effected using a variety of conditions such as pentafluorobenzyl alcohol, triphenylphosphine and diisopropyl azodicarboxylate to introduce the substituted piperazine 7. Alternatively, the reaction may be effected in the presence of diisopropylethylamine and bromoacetonitrile.

The compound of formula (I) 8 is readily modified on the indole nitrogen using conventional methodology. Thus, for example, where $R^2$ is an alkyl group, reaction with an appropriate alkyl halide in the presence of a hydride, affords further compounds of formula (I) 9.

The indole-3-acetic acid intermediates 6 (where n=1) may be prepared by the general route outlined in Scheme 2 or by methods analogous thereto. Thus, an appropriately substituted α-oxo-indole-3-acetyl chloride 10 may be converted to the corresponding ester by reaction with, for example, ethanol, in the presence of a base, such as triethylamine. The resultant α-oxo ester is then reduced using, for example, catalytic hydrogenation using a transition metal catalyst such as palladium on carbon, followed by hydrolysis using, for example, a hydroxide such as sodium hydroxide, to afford the acetic acid compound 6.

The indole-3-propanoic acid intermediates 6 (where n=2) may be prepared by the general route outlined in Scheme 3 or by methods analogous thereto. Thus, an appropriately substituted δ-oxopentanoic acid 1 (where n=2) may be reacted with phenyl hydrazine or with a mono- or disubstituted phenyl hydrazine under conventional conditions for the Fischer indole synthesis or by heating the mixture at reflux in the presence of trifluoroacetic acid. The reaction is conveniently effecting in a solvent, for example, triethylamine.

Other indole-3-carboxylic acids in which n is 3 or 4 may be prepared by methods analogous to those described in Scheme 3 or by other methods well known to a person of ordinary skill in the art.

The piperazine intermediates 7 (where $R^5$=substituted phenyl) may be prepared by the general route outlined in Scheme 4 or by methods analogous thereto. Thus, an appropriately substituted phenyl halide 11 may be coupled to a protected piperazine derivative 12 using conventional coupling conditions such as mixing with sodium or potassium tert-butoxide, to which mixture is added (RS)-2,2'-bis(diphenylphosphino)-1,1'-binaphthyl and tris(dibenzylideneacetone)dipalladium (0). The reaction is conveniently effected in an aromatic hydrocarbon solvent such as toluene. Deprotection of the phenylpiperazine compound may be effected in a conventional manner, for example, by treatment with an organic acid such as trifluoroacetic acid or an inorganic acid, such as hydrochloric acid to afford an amine 7, where $R^5$ is a substituted phenyl group.

Other piperazine intermediates 7 in which $R^5$ is other than a substituted phenyl group may be prepared by methods analogous to those described in Scheme 4 or by other methods well known to a person of ordinary skill in the art.

In an alternative method, compounds of the present invention in which X=O may be prepared by the general route outlined in Scheme 5 or by methods analogous thereto. A 2-aryl-indole-3-carboxylic acid intermediate 14 may be coupled to a piperazine intermediate 7 using conventional coupling conditions such as treating the carboxylic acid with 1,1-carbonyldiimidazole, followed by reaction with the piperazine. The reaction is conveniently effected in a suitable solvent such as an ether, for example, tetrahydrofuran. The treatment with CDI is preferably effected at the reflux temperature of the solvent whereas reaction with the piperazine is preferably effected at about room temperature.

Alternative coupling conditions comprise mixing the 2-aryl-indole-3-carboxylic acid 14 and the piperazine 7 with 1-hydroxybenzotriazole, followed by addition of 1-(3-dimethylaminopropyl)-3-ethylcarbodiimide hydrochloride. The reaction is conveniently effected in a suitable solvent such as an ether, for example, tetrahydrofuran, and preferably at about room temperature, to afford the compound of formula (I) 9.

In a further alternative method, compounds of the present invention in which X=O may be prepared by the general route outlined in Scheme 6 or by methods analogous thereto. An indole-3-carboxylic acid 15 may be coupled to a piperazine intermediate 7, according to the general methods described in relation to Scheme 5. The resultant intermediate indole may then be brominated at the 2-position by treatment with a suitable brominating agent such as bromotrimethylsilane. The reaction is preferably effected in a suitable organic solvent such as dimethylsulfoxide, conveniently at about room temperature, to afford the 2-bromo-indole intermediate 16.

Reaction of the 2-bromo-indole 16 with an appropriate aryl boronic acid using the conventional conditions of a Suzuki coupling, for example, using a catalyst such as [1,4-butanediylbis(diphenylphosphine)]-dichloropalladium. The reaction is preferably effected in the presence of an alkali metal carbonate such as aqueous sodium carbonate and at an elevated temperature, for example, between 70° C. and 95° C., to afford the compound of formula (I) 8.

The boronic acids of use in the coupling described in Scheme 6 are commercially available or may be prepared by methods well known to a person of ordinary skill in the art.

In another alternative method, compounds of the present invention in which X=O may be prepared by the general route outlined in Scheme 7 or by methods analogous thereto. Thus, a 2-aryl-indole-3-carboxylic acid 17 may be reacted with a mono-protected piperazine 18 to afford the N-protected intermediate 19. The coupling may be effected according to the general methods described in relation to Scheme 5. The resultant N-protected piperazine 19 may then be deprotected using acidic conditions, for example, trifluoroacetic acid and then N-substituted using a variety of reagents of the formula $R^5$-Hal where Hal is a halogen atom, preferably bromine or chlorine. The reaction is preferably effected in the presence of an inorganic base such as potassium carbonate, conveniently in a solvent such as an ester, for example, acetone, conveniently at room temperature.

This method is particularly useful for the preparation of compounds of the present invention in which $R^5$ is an alkyl, cycloalkyl, cycloalkylalkyl, alkenyl, aryl, heteroaryl, aralkyl or heteroaralkyl group.

The halides of formula $R^5$-Hal of use in the methods described in Scheme 7 are commercially available or may be prepared by methods well known to a person or ordinary skill in the art.

It will be appreciated that, where appropriate, a combination of the general methodology described in Schemes 1 to 7 may be applied to prepare further compounds of the present invention.

The compounds of formula (I) prepared according to the methods described above may be isolated and purified in a conventional manner, for example, extraction, precipitation, fractional crystallization, recrystallization, chromatography or a combination thereof.

Although the reaction schemes described herein are reasonably general, it will be understood by those skilled in the art of organic synthesis that one or more functional groups present in a given compound of formula (I) may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out in U.S. Pat. Nos. 5,472,978, 5,495,047 and 5,610,183. The compounds were found to be active with $IC_{50}$ at the $NK_1$ receptor of less than 100 nM in said test method.

The following non-limiting Examples serve to illustrate the preparation of compounds of the present invention:

Description 1

Scavenger Resin

A solution of pentafluorophenyl chlorothionoformate (0.5 M) and dilsopropylethylamine (0.5 M) in tetrahydrofuran-dichloromethane (1:1, 20 mL per 1 gram of resin) was added to aminomethylated polystyrene HL resin (Novabiochem, product no. 01-64-0010) and the mixture was stirred at room temperature for 1 h. The resin was washed with tetrahydrofuran-dichloromethane (1:1, 4×) and dimethylformamide (4×), then a solution of triethylamine in dimethylformamide (0.5M, 20 mL per 1 g of resin) was added. The mixture was stirred at room temperature for 30 min., then the resin was washed with dimethylformamide (4×), tetrahydrofuran-dichloromethane (1:1, 4×), dichloromethane (4×) and ether (2×). The resin was then dried in vacuo for 1 h. and used immediately.

Description 2

Loaded Resin 1,3-Diisopropylcarbodiimide (3.47 g) was added to 4-bromo-δ-oxobenzenepentanoic acid (*J. Org. Cheni.* 1948, 13, 284; *J. Org. Chein.* 1984, 49, 3170; 14.91 g) in dichloromethane (55 mL) and the mixture was stirred at room temperature for 30 min. The mixture was added to 4-sulfamylbutyryl AM resin (Novabiochem, product no. 01-64-0152, 1 mmol/g loading, 5.5 g), 4-dimethylaminopyridine (671 mg) was added and the mixture was stirred at room temperature for 18 h. The mixture was filtered and the resin was washed with dimethylformamide (50 mL), dichloromethane (50 mL), methanol (50 mL) and ether (50 mL) and dried in vacuo. A dispersion of (4-methylphenyl)hydrazine hydrochloride (9.2 g) in glacial acetic acid (135 mL) then zinc chloride (10.8 g) were added and the mixture was heated to 75° C. for 18 h. The mixture was cooled to room temperature, filtered and washed with glacial acetic acid-tetrahydrofuran (1:1, 50 mL), dichloromethane (50 mL), dimethylformamide (50 mL), methanol (50 mL) and ether (50 mL) and dried in vacuo.

Description 3

Determination of Resin Loading by Preparation of N,N-Dimethyl-[2-(4-bromophenyl)-5-methyl-1H-indol-3-yl]propanamide Diisopropylethylamine (65 mg) and bromoacetonitrile (288 mg) were added to the resin of Description 2 (100 mg) in N-methylpyrrolidinone (1 mL) and the mixture was allowed to stand at room temperature for 18 h. The mixture was filtered and the resin was washed with N-methylpyrrolidinone (5 mL) and tetrahydrofuran (5 mL). A solution of dimethylamine in tetrahydrofuran (2M, 2 mL) was added and the mixture was allowed to stand at room temperature for 18 h. The mixture was filtered and the filtrate was collected. The solvent was evaporated under reduced pressure and the residue was dried in vacuo to give the title compound as a pale brown solid (20 mg), consistent with a resin loading of 0.52 mmol/g prior to activation and cleavage.

Description 4

Ethyl 5-Methyl-α-oxo-2-phenyl-1H-indole-3-acetate

5-Methyl-α-oxo-2-phenyl-1H-indole-3-acetyl chloride (Ind. J. Chem. Sec. B. 1995, 796–801; 2.5 g, 12 mmol) was added to a solution of triethylamine (25 mL) in ethanol (150 mL). The solvent was evaporated under reduced pressure, water was added and the mixture was extracted with ethyl acetate. The combined organic fractions were dried ($MgSO_4$) and the solvent was evaporated under reduced pressure to give the title compound as a pale brown solid (3.8 g, 98%). $^1$H NMR (250 MHz, $CDCl_3$) δ1.03 (3H, t, J 7 Hz), 2.53 (3H, s), 3.60–3.84 (2H, m), 7.18–7.20 (1H, m), 7.30–7.35 (2H, m), 7.40–7.57 (5H, m), and 8.23 (1H, s).

Description 5

Ethyl 5-Methyl-2-phenyl-1H-indole-3-acetate

A suspension of palladium on carbon (10%, 1 g) in dioxane (50 mL) was added to a solution of ethyl 5-methyl-α-oxo-2-phenyl-1H-indole-3-acetate (Description 4, 3.66 g) in dioxane (250 mL). A solution of sodium hypophosphite (10 g) in water (10 mL) was added and the mixture was heated under reflux for 10 h. Further palladium on carbon (10%, 1 g) and sodium hypophosphite (10 g) were added and the mixture was heated under reflux for 24 h. Further palladium on carbon (10%, 1 g) and sodium hypophosphite (10 g) were added and the mixture was heated under reflux for 24 h. The mixture was cooled, filtered through celite and the solvent was evaporated under reduced pressure. The residue was purified by flash column chromatography on silica gel eluting with hexane/EtOAc (90:10) to give the title compound as a colourless solid (1.6 g, 47%). $^1$H NMR (360 MHz, $CDCl_3$) δ0.86 (3H, t, J 7 Hz), 2.43 (3H, s), 3.73 (2H, s), 4.11–4.16 (2H, m), 6.96 (1H, dd, J 8, 1.8 Hz), 7.18 (1H, d, J 10.8 Hz), 7.28–7.46 (5H, m), 7.58 (1H, d, J 7.2 Hz), and 7.98 (1H, br s). m/z ($ES^+$) 294 (M+1).

Description 6

5-Methyl-2-phenyl-1H-indole-3-acetic Acid

Aqueous sodium hydroxide (4M, 75 mL) was added to ethyl 5-methyl-2-phenyl-1H-indole-3-acetate (Description 5, 1.61 g) in methanol (150 mL) and the mixture was stirred at room temperature for 2 h. The mixture was cooled to 0° C., the pH was adjusted to 3.0 with hydrochloric acid (2M) and the mixture was extracted with ethyl acetate. The combined organic fractions were dried ($MgSO_4$) and the solvent was evaporated under reduced pressure. The residue was recrystallized from ether to give the title compound as a colourless solid (1.1 g, 76%). $^1$H NMR (360 MHz, $CDCl_3$) δ2.47 (3H, s), 3.85 (3H, s), 7.05 (1H, dd, J 8.3, 1.4 Hz), 7.27 (1H, d, J 11.2 Hz), 7.36–7.49 (4H, m), 7.62 (1H, d, J 9.2 Hz), and 8.05 (1H, br s). m/z ($ES^+$) 266 (M+1).

Description 7

5-Methyl-2-phenyl-1H-indole-3-propanoic Acid

Triethylamine (1.4 mL, 10 mmol) was added to a stirred suspension of δ-oxobenzenepentanoic acid (1.92 g, 10 mmol) and (4-methylphenyl)hydrazine hydrochloride (1.59 g, 10 mmol) in ethanol (16 mL) and the mixture was stirred at room temperature for 4 h. Ether (100 mL) was added, the mixture was filtered and the solvent was evaporated under reduced pressure. The residue was added slowly to trifluoroacetic acid (15 mL) and the mixture was heated under reflux for 2 h. The mixture was cooled, water (100 mL) was added and the mixture was extracted with ethyl acetate (100 mL). The organic fraction was washed with brine (30 mL), dried ($MgSO_4$) and the volume was reduced to Ca. 10 mL by evaporation under reduced pressure. The precipitate was collected and recrystallized from ether to give the title compound as a pale solid (1.51 g, 54%). $^1$H NMR (360 MHz, DMSO-$d_6$) δ2.39 (3H, s), 2.50–2.58 (2H, m), 3.03–3.09 (2H, m), 6.91–6.95 (1H, m), 7.23–7.25 (1H, m), 7.34–7.40 (2H, m), 7.47–7.63 (4H, m), 11.4 (1H, br s), and 12.25 (1H, br s). m/z ($ES^+$) 280 (M+1).

Description 8

5-Chloro-2-phenyl-1H-indole-3-propanoic Acid

Prepared from δ-oxobenzenepentanoic acid and (4-chlorophenyl)hydrazine hydrochloride according to the method of Description 7. $^1$H NMR (360 MHz, $CDCl_3$) (Contains 20% δ-oxobenzenepentanoic acid) δ8.02 (1H, s), 7.52–7.33 (6H, m), 7.23–7.18 (1H, m), 7.10–7.07 (1H, m), 3.16–3.11 (2H, m), and 2.65–2.60 (2H, m).

Description 9

5-Fluoro-2-phenyl-1H-indole-3-propanoic Acid

Prepared from δ-oxobenzenepentanoic acid and (4-fluorophenyl)hydrazine hydrochloride according to the method of Description 7. $^1$H NMR (360 MHz, $CDCl_3$) (Contains 40% δ-oxobenzenepentanoic acid) δ8.04 (1H, s), 7.56–7.39 (5H, m), 7.30–7.25 (2H, m), 6.98–6.93 (1H, m), 3.23–3.18 (2H, m), and 2.71–2.67 (2H, m).

Description 10

5,6-Dimethyl-2-phenyl-1H-indole-3-propanoic Acid and 4,5-Dimethyl-2-phenyl-1H-indole-3-propanoic Acid Prepared from δ-oxobenzenepentanoic acid and (3,4-dimethylphenyl)hydrazine hydrochloride according to the method of Description 7 as a 2:1 mixture of isomers. $^1$H NMR (360 MHz, $CDCl_3$) (Contains 29% δ-oxobenzenepentanoic acid); 5,6-dimethyl-2-phenyl-1H-indole-3-propanoic acid (Major Isomer) δ7.85 (1H, s), 7.58–7.33 (5H, m), 7.37 (1H, s), 7.16 (1H, s), 3.25–3.20 (2H, m), 2.75–2.67 (2H, m), and 2.38 (6H, s); 4,5-dimethyl-2-phenyl-1H-indole-3-propanoic acid (Minor Isomer) δ7.92 (1H, s), 7.58–7.33 (5H, m), 7.12 (1H, t, J 8.2 Hz), 7.02 (1H, t, J 8.2 Hz), 3.35–3.31 (2H, m), 2.75–2.67 (2H, m), 2.64 (3H, s), and 2.39 (3H, s).

Description 11

5-Chloro-2-(4-chlorophenyl)-1H-indole-3-propanoic Acid

Prepared from 4-chloro-δ-oxobenzenepentanoic acid and (4-chlorophenyl)hydrazine hydrochloride according to the method of Description 7. $^1$H NMR (250 MHz, DMSO-$d_6$) δ2.55–2.61 (2H, m), 3.07–3.13 (2H, m), 7.16 (2H, d, J 12.6 Hz), 7.41 (2H, d, J 12.6 Hz), 7.62–7.71 (3H, m), 11.52 (1H, br s), and 12.19 (1H, br s). m/z (ES$^+$) 331, 333 (M+1).

Description 12

5-Chloro-2-(4-chlorophenyl)-1-methyl-1H-indole-3-propanoic Acid

Sodium hydride (60% suspension in mineral oil, 5.98 g) was added in portions to a stirred, cooled (0° C.) solution of 5-chloro-2-(4-chlorophenyl)-1H-indole-3-propanoic acid (Description 11, 10 g, 30 mmol) in dimethylformamide (100 mL) and the mixture was stirred at 0° C. for 30 min. Iodomethane (9 mL) was added and the mixture was stirred at room temperature for 30 min. Water (1.5 L) was added and the mixture was extracted with ether (3×400 mL). The combined organic fractions were dried (MgSO$_4$) and the solvent was evaporated under reduced pressure. The residue was dissolved in methanol (240 mL) and aqueous sodium hydroxide (4M, 60 mL) was added. The mixture was heated under reflux for 1 h., cooled and the pH was adjusted to 1.0 with hydrochloric acid (2M). The layers were separated and the aqueous layer was extracted with ethyl acetate. The combined organic fractions were dried (MgSO$_4$) and the solvent was evaporated under reduced pressure. The residue was triturated with hexane and the solid was collected and dried in vacuo to give the the title compound (7.5 g, 72%). $^1$H NMR (360 MHz, CDCl$_3$) δ2.54–2.59 (2H, m), 2.96–3.00 (2H, m), 3.53 (3H, s), 7.18–7.30 (4H, m), 7.44–7.48 (2H, m), and 7.58 (1H, d, J 1.8 Hz).

Description 13

Loaded Resin 1,3-Diisopropylcarbodiimide (1.21 g) was added to 5-chloro-2-(4-chlorophenyl)-1H-indole-3-propanoic acid (Description 11, 6.4 g, 19.2 mmol) in tetrahydrofuran-dichloromethane (1:1, 80 mL) and the mixture was stirred at room temperature for 30 min. The mixture was added to 4-sulfamylbutyryl AM resin (Novabiochem, product no. 01-64-0152, 1 mmol/g loading, 8.3 g), 4-dimethylaminopyridine (292 mg) was added and the mixture was stirred at room temperature for 16 h. The mixture was filtered and the resin was washed 20 with tetrahydrofuran-dichloromethane (1:1), methanol (50 mL) and tetrahydrofuran (3×) and dried in vacuo.

Description 14

Determination of Resin Loading by preparation of N,N-Dimethyl-[2-(4-bromophenyl)-5-methyl-1H-indol-3-yl]propanamide The loading of the resin of Description 13 was determined to be 0.51 mmol/g by the method of Description 3.

Description 15

2-Bromo-4-(trifluoromethoxy)phenol

A solution of bromine (32 g, 0.2 mol) in chloroform (50 mL) was added dropwise to a stirred, cooled (0° C.) solution of 4-(trifluoromethoxy)phenol (35.6 g, 0.2 mol) in chloroform (280 mL). The mixture was stirred at 0° C. for 1 h. and at room temperature for 2 h. Dichloromethane (200 mL) and water (400 mL) were added and the layers were separated. The organic fraction was washed with water (400 mL) and brine (200 mL), dried (MgSO$_4$) and the solvent was evaporated under reduced pressure. The residue was purified by distillation under reduced pressure to give the title compound as a colorless oil. $^1$H NMR (250 MHz, CDCl$_3$) δ7.38 (1H, d, J 2.1 Hz), 7.13 (1H, dd, J 9.1, 2.1 Hz), 7.03 (1H, d, J 9.1 Hz), and 5.53 (1H, s).

Description 16

2-Bromo-1-methoxy-4-(trifluoromethoxy)benzene

Iodomethane (14.94 mL, 0.24 mol) was added to a solution of 2-bromo-4-(trifluoromethoxy)phenol (Description 15, 7.2 g) and potassium carbonate (11.6 g, 0.084 mol) in dimethylformamide (60 mL) and the mixture was stirred at room temperature for 15 h. Water (400 mL) and ether (200 mL) were added and the layers were separated. The organic fraction was washed with water (4×200 mL), saturated aqueous sodium hydrogen carbonate (2×200 mL) and brine (200 mL), dried (MgSO$_4$) and the solvent was evaporated under reduced pressure. The residue was purified by flash column chromatography on silica gel, eluting with hexane/EtOAc (100:0 increasing to 98:2), to give the title compound. $^1$H NMR (250 MHz, CDCl$_3$) δ7.45 (1H, d, J 2.8 Hz), 7.16 (1H, dd, J 9.0, 2.8 Hz), 6.88 (1H, d, J 9.0 Hz), and 3.90 (3H, s).

Description 17

1,1-Dimethylethyl 4-[2-Methoxy-4-(trifluoromethoxy)phenyl]-1-piperazinecarboxylate A solution of 2-bromo-1-methoxy4-(trifluoromethoxy)benzene (Description 16, 3 g, 11 mmol), 1,1-dimethylethyl 1-piperazinecarboxylate (2.47 g) and sodium tert-butoxide (1.49 g) in toluene (100 mL) was degassed with bubbling argon. (RS)-2,2'-Bis(diphenylphosphino)-1,1'-binaphthyl (56 mg) and tris(dibenzylideneacetone)dipalladium (0) (13.8 mg) were added and the mixture was degassed and stirred at 80° C. for 72 h. The mixture was cooled, diluted with ether (150 mL) and filtered through celite. The solvent was evaporated under reduced pressure and the residue was purified by flash column chromatography on silica gel, eluting with hexane/EtOAc (95:5 increasing to 85:15), to give the title compound (3.4 g, 82%). $^1$H NMR (250 MHz, CDCl$_3$) δ1.48 (9H, s), 2.98–3.01 (4H, m), 3.58–3.61 (4H, m), 3.87 (3H, s), and 6.74–6.85 (3H, m). m/z (ES$^+$) 377 (M+1).

Description 18

1-[2-Methoxy-4-(trifluoromethoxy)phenyl]piperazine

Trifluoroacetic acid (90 mL) was added to a stirred, cooled (0° C.) solution of 1,1-dimethylethyl 4-[2-methoxy-4-(trifluoromethoxy)phenyl]-1-piperazinecarboxylate (Description 17, 3.4 g) in dichloromethane (135 mL) and the mixture was stirred at room temperature for 1 h. The mixture was allowed to warm to room temperature, saturated aqueous sodium bicarbonate solution (380 mL) was added and the mixture was extracted with dichloromethane. The combined organic fractions were dried (MgSO$_4$) and the solvent was evaporated under reduced pressure to give the title compound as a pale brown solid (1.84 g, 74%). $^1$H NMR (250 MHz, CDCl$_3$) δ3.28–3.58 (8H, m), 3.87 (3H, s), 6.77 (1H, d, J 1.9 Hz), 6.84 (1H, d, J 8.9 Hz), and 6.91–6.95 (1H, m).

Description 19

1-[2-(Trifluoromethoxy)phenyl]piperazine Hydrochloride

A solution of 1-iodo-2-(trifluoromethoxy)benzene (23.2 g, 80.6 mmol), 1,1-dimethylethyl 1-piperazinecarboxylate (10 g, 53.7 mmol) and sodium tert-butoxide (7.2 g, 75.2 mmol) in toluene was degassed with bubbling nitrogen. (RS)-2,2'-Bis(diphenylphosphino)-1,1'-binaphthyl (334 mg, 0.54 mmol) and tris(dibenzylideneacetone)dipalladium (0) (492 mg, 0.54 mmol) were added, and the mixture was degassed and stirred at 80° C. for 48 h. The mixture was cooled, poured into water and extracted with ethyl acetate. The combined organic fractions were dried (MgSO$_4$), filtered through a plug of silica gel, eluting with ethyl acetate, and the solvent was evaporated under reduced pressure. The residue was dissolved in ethyl acetate (200 mL), hydrochloric acid (5M, 100 mL) was added and the mixture was stirred at room temperature overnight. The layers were separated and the organic layer was extracted with hydrochloric acid (5M). The combined aqueous extracts were washed with ether, basified with aqueous sodium hydroxide (4N) and extracted with ethyl acetate. The combined organic fractions were dried (MgSO$_4$) and the solvent was evaporated under reduced pressure. The residue was dissolved in ethyl acetate-ether (1:1) and ethereal hydrogen chloride (1M, 40 mL) was added. The solid was collected and dried in vacuo to give the title compound as a light brown solid (9.5 g, 62%). $^1$H NMR (360 MHz, D$_2$O) δ7.41–7.35 (2H, m), 7.26–7.19 (2H, m), 3.45–3.42 (4H, m), and 3.34–3.32 (4H, m). m/z (ES$^+$) 247 (M+1).

Description 20

1,1-Dimethylethyl 4-[3-(Phenylmethoxy)phenyl]-1-piperazinecarboxulate

Prepared from 1-iodo-3-(phenylmethoxy)benzene and 1,1-dimethylethyl 1-piperazinecarboxylate according to the method of Description 17. m/z (ES$^+$) 369 (M+1).

Description 21

1,1-Dimethylethyl 4-(3-Hydroxyphenyl)-1-piperazinecarboxylate

A slurry of palladium hydroxide on carbon (330 mg) in methanol (10 mL) was added to a solution of 1,1-dimethylethyl 4-[3-(phenylmethoxy)phenyl]-1-piperazinecarboxylate (Description 20, 3.25 g, 8.8 mmol) in ethyl acetate/methanol (1:9) and the mixture was shaken under an atmosphere of hydrogen (40 psi) for 48 h. The mixture was filtered through celite and the solvent was evaporated under reduced pressure to give the title compound (2.28 g, 93%). $^1$H NMR (360 MHz, CDCl$_3$) δ1.48 (9H, s), 3.10–3.13 (4H, m), 3.54–3.57 (4H, m), 6.34 (1H, dd, J 7.9, 2.2 Hz), 6.41 (1H, t, J 2.0 Hz), 6.34 (1H, dd, J 8.3, 2.2 Hz), and 7.11 (1H, t, J 7.9 Hz).

Description 22

1-(3-Ethoxyphenyl)piperazine

Bromoethane (0.7 mL) was added to a mixture of 1,1-dimethylethyl 4-(3-hydroxyphenyl)-1-piperazinecarboxylate (Description 21, 500 mg, 1.8 mmol) and potassium carbonate (495 mg) in acetone (50 mL) and the mixture was heated under reflux for 13 h. The mixture was cooled, water (100 mL) was added and the mixture was extracted with ether (3×100 mL). The combined organic fractions were dried (MgSO$_4$) and the solvent was evaporated under reduced pressure. The residue was purified by flash column chromatography on silica gel, eluting with hexane/EtOAc (95:5). The residue was dissolved in dichloromethane (14 mL), cooled to 0° C. and trifluoroacetic acid (9 mL) was added. The mixture was stirred at 0° C. for 1 h., then allowed to warm to room temperature and saturated aqueous sodium bicarbonate solution (40 mL) was added. The mixture was extracted with dichloromethane, the combined organic fractions were dried (MgSO$_4$) and the solvent was evaporated under reduced pressure to give the title compound as a pale brown solid (210 mg, 46%). $^1$H NMR (250 MHz, CDCl$_3$) δ1.43 (3H, t, J 7.6 Hz), 3.65–3.82 (8H, m), 3.98–4.13 (2H, m), 6.84–6.91 (2H, m), and 7.34–7.40 (1H, m).

Description 23

1-[3-(1-Methylethoxy)phenyl]piperazine

Prepared from 1,1-dimethylethyl 4-(3-hydroxyphenyl)-1-piperazinecarboxylate (Description 21) and 2-iodopropane according to the method of Description 22. $^1$H NMR (250 MHz, CDCl$_3$) δ1.34 (6H, d, J 6 Hz), 3.63–3.78 (8H, m), 4.51–4.60 (1H, m), 6.78–6.84 (2H, m), and 7.30–7.37 (1H, m).

Description 24

5-Methyl-1H-indole-3-propanoic Acid

Acrylic acid (16.5 mL, 240.6 mmol) was added to a solution of 5-methyl-1H-indole (10.5 g, 80.2 mmol) in acetic acid (20 mL) and acetic anhydride (20 mL) and the mixture was stirred at room temperature for 1 week. Aqueous sodium hydroxide (4N, 100 mL) was added and the mixture was washed with ethyl acetate. The aqueous fraction was acidified to pH 1 with hydrochloric acid (5M) and extracted with ethyl acetate. The combined organic fractions were dried (MgSO$_4$) and the solvent was evaporated under reduced pressure to give the title compound as a brown solid (7 g, 43%). $^1$H NMR (360MHz, CDCl$_3$) δ7.85 (1H, br s), 7.38 (1H, s), 7.24 (1H, d, J 8.3 Hz), 7.02 (1H, dd, J 8.3, 2.3 Hz), 6.97 (1H, d, J 2.3 Hz), 3.09 (2H, t, J 7.6 Hz), 2.76 (2H, t, J 7.6 Hz), and 2.46 (3H, s).

Description 25

1-[3-(1H-Indol-3-yl)-1-oxopropyl]-4-(2-methoxyphenyl)piperazine

Triethylamine (1.46 mL, 10.5 mmol) was added to a mixture of 1H-indole-3-propanoic acid (1.36 g, 7.2 mmol), 1-(2-methoxyphenyl)piperazine hydrochloride (1.5 g, 6.55 mmol) and 1-hydroxybenzotriazole (1.33g, 7.86 mmol) in tetrahydrofuran (20 mL) and the mixture was stirred at room temperature for 10 min. 1-(3-Dimethylaminopropyl)-3-ethyl carbodiimide hydrochloride (1.89 g, 9.8 mmol) was added and the mixture was stirred at room temperature for 2 h. The mixture was poured into water and extracted with ethyl acetate. The combined organic fractions were washed with saturated aqueous sodium carbonate and water, dried (MgSO$_4$), and the solvent was evaporated under reduced pressure. The residue was triturated with hexane to give the title compound as a colorless solid (2.1 g, 88%). $^1$H NMR (360 MHz, CDCl$_3$) δ8.00 (1H, br s), 7.63 (1H, d, J 7.6 Hz), 7.36 (1H, d, J 8.0 Hz), 7.10–7.00 (2H, m), 6.94–6.80 (3H, m), 3.85 (3H, s), 3.80 (2H, t, J 5.0 Hz), 3.52 (2H, t, J 5.0 Hz), 3.14 (2H, m), 2.95 (2H, t, J 5.0 Hz), and 2.77 (4H, m). m/z (ES$^+$) 364 (M+1).

Description 26

4-(2-Methoxyphenyl) 1-[3-(5-methyl-1H-indol-3-yl)-1-oxopropyl]piperazine

Prepared from 5-methyl-1H-indole-3-propanoic acid (Description 24) and-(2-methoxyphenyl)piperazine hydrochloride according to the method of Description 25. $^1$H NMR (360 MHz, CDCl$_3$) δ7.89 (1H, br s), 7.40 (1H, s), 7.24 (1H, d, J 8.3 Hz), 7.04–7.00 (3H, m), 6.94–6.81 (3H, m), 3.86 (3H, s), 3.81 (2H, t, J 5.0 Hz), 3.53 (2H, t, J 5.0 Hz), 3.13 (2H, t, J 7.6 Hz), 2.96 (2H, t, J 5.0 Hz), 2.80 (2H, t, J 5.0 Hz), 2.77–2.73 (2H, m), and 2.46 (3H, s).

Description 27

1-[3-(2-Bromo-1H-indol-3-yl)-1-oxopropyl]-4-(2-methoxyphenyl)piperazine

A solution of bromotrimethylsilane (0.27 mL, 2.62 mmol) in dimethylsulfoxide (5 mL) was added dropwise to a solution of 1-[3-(1-indol-3-yl)-1-oxopropyl]-4-(2-methoxyphenyl)piperazine (Description 25, 0.5 g, 1.38 mmol) in dimethylsulfoxide (10 mL) and the mixture was stirred at room temperature for 2 h. The mixture was poured into saturated aqueous sodium hydrogen carbonate and extracted with ethyl acetate. The combined organic fractions were washed with water, dried (MgSO$_4$), and the solvent was evaporated under reduced pressure. The residue was purified by flash column chromatography on silica gel, eluting with hexane/EtOAc (40:60) to give the title compound as a colorless solid (415 mg, 68%). $^1$H NMR (360 MHz, CDCl$_3$) δ8.09 (1H, br s), 7.56 (1H, d, J 8.1 Hz), 7.27 (1H, m), 7.19–7.12 (2H, m), 7.01 (1H, dd, J 1.6, 7.7 Hz), 6.93–6.85 (2H, m), 6.80 (1H, dd, J 1.6, 7.8 Hz), 3.85 (3H, s), 3.79 (2H, t, J 5.0 Hz), 3.48 (2H, m), 3.12 (2H, m), 2.90 (2H, t, J 5.0 Hz), 2.76 (2H, t, J 5.0 Hz), and 2.69 (2H, m). m/z (ES$^+$) 442, 444 (M+1).

Description 28

1-[3-(2-Bromo-5-methyl-1H-indol-3-yl)-1-oxopropyl]-4-(2-methoxyphenyl)piperazine Prepared from 4-(2-methoxyphenyl)-1-[3-(5-methyl-1H-indol-3-yl)-1-oxopropyl]piperazine (Description 26) according to the method of Description 27. $^1$H NMR (360 MHz, CDCl$_3$) δ7.96 (1H, br s), 7.34 (1H, s), 7.16 (1H, d, J 8.3 Hz), 7.04–6.98 (2H, m), 6.93–6.80 (3H, m), 3.86 (3H, s), 3.80 (2H, t, J 5.0 Hz), 3.50 (2H, t, J 5.0 Hz), 3.08 (2H, m), 2.93 (2H, t, J 5.0 Hz), 2.79 (2H, t, J 5.0 Hz), 2.67 (2H, m), and 2.38 (3H, s). m/z (ES$^+$) 456, 458 (M+1).

Description 29

[2-Methoxy-5-(trifluoromethoxy)phenyl]boronic Acid n-Butyllithium (1.6M in hexanes, 3.8 mL, 6 mmol) was added dropwise to a cooled (−78° C.) solution of 2-bromo-1-methoxy-4-(trifluoromethoxy)benzene (Description 16, 1.5 g, 5.5 mmol) in tetrahydrofuran (prefiltered through alumina, 18 mL) [internal temperature <−70° C.]. The mixture was stirred at −78° C. for 15 min., then trimethylborate (2 mL, 17.6 mmol) was added dropwise [internal temperature <−70° C.]. The mixture was stirred at −78° C. for 30 min., then hydrochloric acid (1M, 6 mL) was added. The mixture was warmed to room temperature and stirred for 30 min. Water (25 mL) was added and the mixture was extracted with ethyl acetate (2×40 mL). The combined organic fractions were washed with water (20 mL) and brine (20 mL), dried (MgSO$_4$) and the solvent was evaporated under reduced pressure. The residue was triturated with hexane and the solid was collected and dried in vacuo at 40° C. to give the title compound as an off white solid (366 mg, 28%). $^1$H NMR (360 MHz, CDCl$_3$) δ3.93 (3H, s), 5.84 (2H, s), 6.90 (1H, d, J 9.0 Hz), 7.29 (1H, m) and 7.70 (1H, J 2.6 Hz).

Description 30

1-{3-[5-Chloro-2-(4-chlorophenyl)-1H-indol-3-yl]-1-oxopropyl}piperazine

Trifluoroacetic acid (20 mL) was added to a stirred, cooled (0° C.) solution of 1,1-dimethylethyl 4-{3-[5-chloro-2-(4-chlorophenyl)- 1-indol-3-yl]-1-oxopropyl}-1-piperazinecarboxylate (Example 80, 600 mg) in dichloromethane (30 mL) and the mixture was stirred at 0° C. for 1 h. The mixture was allowed to warm to room temperature, saturated aqueous sodium bicarbonate solution (80 mL) was added and the mixture was extracted with dichloromethane. The combined organic fractions were dried (MgSO$_4$) and the solvent was evaporated under reduced pressure to give the title compound as a pale solid (390 mg, 81%). $^1$H NMR (360 MHz, CD$_3$OD) δ2.65–2.69 (4H, m), 2.91–2.95 (2H, m), 3.23–3.28 (2H, m), 3.44–3.47 (2H, m), 3.71–3.75 (2H, m), 7.12 (1H, dd, J 8.7, 2.1 Hz), 7.35 (1H, d, J 7.9 Hz), and 7.46–7.58 (5H, m). m/z (ES$^+$) 402, 404 (M+1).

Description 31

1-{3-[5-Chloro-2-(4-chlorophenyl)-1-methyl-1H-indol-3-yl]-1-oxopropyl}piperazine Prepared from 1,1-dimethylethyl 4-{3-[5-chloro-2-(4-chlorophenyl)-1-methyl-1H-indol-3-yl]-1-oxopropyl}-1-piperazinecarboxylate (Example 95) according to the method of Description 30. $^1$H NMR (360 MHz, CDCl$_3$) δ2.47–2.52 (2H, m), 2.65–2.68 (2H, m), 2.83–2.85 (2H, m), 2.97–3.01 (2H, m), 3.26–3.30 (2H, m), 3.39 (1H, br s), 3.55 (3H, s), 3.59–3.62 (2H, m), 7.19–7.32 (4H, m), 7.49 (2H, d, J 8.3 Hz), and 7.57 (1H, s). m/z (ES$^+$) 416, 418 (M+1).

Description 32

(S)-N-(2-{N-[(1,1-Dimethylethoxy)carbonyl]methylamino}-1-oxo-3-phenylpropyl)glycine methyl ester N-[(1,1-Dimethylethoxy)carbonyl]-N-methyl-L-phenylalanine dicyclohexylamine salt (3.0 g, 6.5 mmol) was partitioned between dichloromethane (100 mL) and aqueous hydrochloric acid (0.1M, 100 mL). The layers were separated and the organic fraction was washed with aqueous hydrochloric acid (0.1M, 100 mL), dried (MgSO$_4$) and the solvent was evaporated under reduced pressure. The residue was dissolved in dichloromethane (30 mL), cooled to 0° C. and N-methylmorpholine (0.72 mL, 0.66 g, 6.5 mmol) then isobutyl chloroformate (0.84 mL, 0.89 g, 6.5 mmol) were added. The mixture was stirred at 0° C. for 10 min., then N-methylmorpholine (0.72 mL, 0.66 g, 6.5 mmol) and glycine methyl ester hydrochloride (0.82 g, 6.5 mmol) were added. The mixture was stirred at 0° C. for 1 h., then at room temperature for 2 h. Water (100 mL) was added and the mixture was extracted with ethyl acetate (100 mL). The organic fraction was dried (MgSO$_4$) and the solvent was evaporated under reduced pressure. The residue was purified by flash column chromatography on silica gel, eluting with hexane/EtOAc (50:50), to give the title compound as a colorless gum (2.28 g, 100%). $^1$H NMR (250 MHz, CDCl$_3$) mixture of two amide rotamers; δ7.28–7.23 (5H, m), 6.66, 6.40 (total 1H, each br s), 5.01, 4.80 (total 1H, each m), 4.24–3.82 (2H, m), 3.75 (3H, s), 3.39 (1H, m), 2.94 (1H, m), 2.81, 2.76 (total 3H, each s), and 1.37, 1.27 (total 9H, each s). m/z (ES$^+$) 351 (M+1).

Description 33

(S)-N-[2-(Methylamino)-1-oxo-3-phenylpropyl] glycine methyl ester

Trifluoroacetic acid (5 mL) was added to a solution of (S)-N-(2-{N-[(1,1-dimethylethoxy)carbonyl] methylamino}-1-oxo-3-phenylpropyl)glycine methyl ester (Description 32, 2.28 g, 6.5 mmol) in dichloromethane (50 mL) and the mixture was stirred at room temperature for 3.5 h. The solvent was evaporated under reduced pressure, then toluene was added and evaporated under reduced pressure. Aqueous sodium carbonate (10%, 100 mL) was added and the mixture was extracted with dichloromethane (2×100 mL). The combined organic fractions were dried (MgSO$_4$) and the solvent was evaporated under reduced pressure. The residue was purified by flash column chromatography on silica gel, eluting with CH$_2$Cl$_2$/MeOH (95:5), to give the title compound as a colorless oil (1.59 g, 98%). $^1$H NMR (250 MHz, CDCl$_3$) δ7.71 (1H, br s), 7.61–7.21 (5H, m), 4.15 (1H, dd, J 18.3, 6.1 Hz), 4.02 (1H, dd, J 18.3, 5.5 Hz), 3.76 (3H, s), 3.25 (2H, m), 2.69 (1H, dd, J 14.7, 10.9 Hz), 2.31 (3H, s), and 1.30 (1H, br s). m/z (ES$^+$) 251 (M+1).

Description 34

(6S)-1-Methyl-6-(phenylmethyl)-2,5-piperazinedione

A solution of (S)-N-[2-(methylamino)-1-oxo-3-phenylpropyl)glycine methyl ester (Description 33, 1.59 g, 6.4 mmol) in toluene (15 mL) was heated at 170° C. in a sealed tube for 42 h. The mixture was cooled, the solvent was evaporated under reduced pressure and the residue was purified by flash column chromatography on silica gel, eluting with CH$_2$Cl$_2$/MeOH/NH$_3$(aq.) (95:5:1), to give the title compound as a colorless solid (1.19 g, 86%). $^1$H NMR (360 MHz, CDCl$_3$) δ7.31 (3H, m), 7.14 (2H, m), 5.93 (1H, br s), 4.16 (1H, m), 3.44 (1H, dd, J 17.0, 3.6 Hz), 3.27 (1H, dd, J 13.9, 3.7 Hz), 3.16 (1H, dd, J 13.9, 4.6 Hz), 3.06 (3H, s), and 2.48 (1H, d, J 17.0 Hz). mI/z (ES$^+$) 218 (M+1).

Description 35

(2S)-1-Methyl-2-(phenylmethyl)piperazine

Lithium aluminium hydride (1.0M in ether, 20.2 mL, 20.2 mmol) was added to a stirred, cooled (0° C.) suspension of (6S)-1-methyl-6-(phenylmethyl)-2,5-piperazinedione (Description 34, 1.1 g, 5.0 mmol) in THF (60 mL) and the mixture was heated under reflux for 1 h. The mixture was cooled to −20° C. and saturated aqueous sodium sulfate (20.2 mL) was added. The mixture was stirred at room temperature for 15 min., filtered and the solvent was evaporated under reduced pressure. The residue was purified by flash column chromatography on silica gel, eluting with CH$_2$C$_2$/MeOH/NH$_3$(aq.) (90:10:1), to give the title compound as a yellow oil (0.83 g, 87%). $^1$H NMR (250 MHz, CDCl$_3$) δ7.31–7.15 (5H, m), 3.17 (1H, dd, J 13.3, 3.9 Hz), 2.92–2.70 (4H, m), 2.46 (2H, m), 2.43 (3H, s), 2.27 (2H, m) and 1.51 (1H, br s). m/z (ES$^+$) 191 (M+1).

EXAMPLE 1

1-{3-[2-(4-Bromophenyl)-5-methyl-1H-indol-3-yl]-1-oxopropyl}-4-(2-methoxyphenyl)piperazine 4-Bromo-δ-oxobenzenepentanoic acid (*J. Org. Chem.* 1948, 13, 284; *J. Org. Chem.* 1984, 49, 3170; 6.2 g, 23 mmol) was added to a solution of 1,3-diisopropylcarbodiimide (1.8 mL, 11.5 mmol) in tetrahydrofuran-dichloromethane (1:1, 40 mL) and the mixture was allowed to stand at room temperature for 20 min. The mixture was added to 4-sulfamylbenzoyl AM resin (Novabiochem, product no. 01-64-0121, 1.15 mmol/g loading; 2 g) in a 70 mL solid phase extraction cartridge equipped with a frit and stopcock. 4-Dimethylaminopyridine (138 mg, 1.1 mmol) was added and the mixture was allowed to stand overnight at room temperature. The resin was washed with tetrahydrofuran-dichloromethane (1:1, 3×), dimethylformamide (3×), dichloromethane (3×) and acetic acid (3×). A solution of (4-methylphenyl)hydrazine hydrochloride (3.2 g, 20 mmol) and zinc chloride (2.7 g, 20 mmol) in glacial acetic acid (40 mL) was added and the mixture was heated to 70° C. for 1 h. The mixture was vented, mixed manually and heated overnight at 70° C. The mixture was cooled and the resin was washed with acetic acid (3×), tetrahydrofuran-dichloromethane (1:1, 3×), dimethylformamide (3×) and tetrahydrofuran-dichloromethane (1:1, 4×). A solution of pentafluorobenzyl alcohol (2.3 g, 11.5 mmol), triphenylphosphine (3 g, 11.5 mmol) and diisopropyl azodicarboxylate (2.3 mL, 11.5 mmol) in tetrahydrofuran-dichloromethane (1:1, 40 mL) was added and the mixture was stirred at room temperature for 3 h. The resin was washed with tetrahydrofuran-dichloromethane (1:1, 4×), dimethylformamide (4×), tetrahydrofuran-dichloromethane (1:1, 4×), dichloromethane (4×) and ether (2×), then dried under a stream of nitrogen and transferred from the cartridge to a round bottom flask. A solution of 1-(2-methoxyphenyl) piperazine (884 mg, 4.6 mmol) in tetrahydrofuran (40 mL) was added and the mixture was left to stand at room temperature for 24 h. Scavenger resin (description 1, 2.4 g) and sufficient tetrahydrofuran to cover the additional swollen resin were added and the mixture was left to stand at room temperature for 24 h. The mixture was filtered and the resin washed with tetrahydrofuran. The combined filtrates were evaporated under reduced pressure and the residue was purified by medium pressure liquid chromatography on silica gel, eluting with hexane-ethyl acetate (1:1) to give the title compound (494 mg, 40%). $^1$H NMR (360 MHz, CDCl$_3$) δ8.00 (1H, br s), 7.59–7.57 (2H, m), 7.45–7.32 (3H, m), 7.27–7.25 (1H, m), 7.06–7.00 (2H, m), 6.93–6.80 (3H, m), 3.85 (3H, s), 3.77 (2H, t, J 5.0 Hz), 3.43 (2H, t, J 5.0 Hz), 3.26 (2H, m), 2.93 (2H, t, J 5.0 Hz), 2.76 (2H, t, J 5.0 Hz), and 2.69 (2H, m). m/z (ES$^+$) 532, 534 (M+1).

The following compounds were prepared according to the method of Example 1, substituting an appropriate keto acid for 4-bromo-δ-oxobenzenepentanoic acid and an appropriate hydrazine for (4-methylphenyl)hydrazine hydrochloride

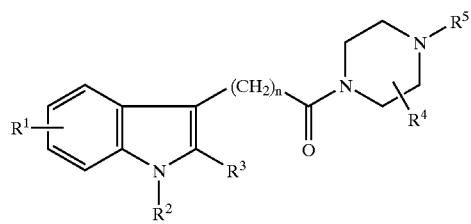

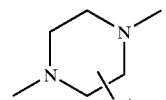

| Ex. | R¹ | R² | R³ | n | R⁴ | R⁵ | Formula | M.W. | m/z (ES⁺) (M + 1) |
|---|---|---|---|---|---|---|---|---|---|
| 2 | 5-Methyl | H | phenyl | 2 | N-Me piperazine | 2-MeO-tolyl | C29H31N3O2 | 453 | 454 |
| 3 | 5-Methyl | H | phenyl | 3 | N-Me piperazine | 2-MeO-tolyl | C30H33N3O2 | 467 | 468 |
| 4 | 5-Methyl | H | phenyl | 4 | N-Me piperazine | 2-MeO-tolyl | C31H35N3O2 | 481 | 482 |
| 5 | 5-Methyl | H | naphthyl | 2 | N-Me piperazine | 2-MeO-tolyl | C33H33N3O2 | 503 | 504 |
| 6 | 5-Methyl | H | naphthyl | 3 | N-Me piperazine | 2-MeO-tolyl | C34H35N3O2 | 517 | 518 |
| 7 | 5-Methyl | H | naphthyl | 4 | N-Me piperazine | 2-MeO-tolyl | C35H37N3O2 | 531 | 532 |
| 8 | 5-Methyl | H | 3-Br-phenyl | 3 | N-Me piperazine | 2-MeO-tolyl | C30H32BrN3O2 | 545 / 547 | 546 / 548 |
| 9 | 5-Methyl | H | 3-Br-phenyl | 4 | N-Me piperazine | 2-MeO-tolyl | C31H34BrN3O2 | 559 / 561 | 560 / 562 |
| 10 | 5-Methyl | H | 4-Br-phenyl | 3 | N-Me piperazine | 2-MeO-tolyl | C30H32BrN3O2 | 545 / 547 | 546 / 548 |
| 11 | 5-Methyl | H | 4-Br-phenyl | 4 | N-Me piperazine | 2-MeO-tolyl | C31H34BrN3O2 | 559 / 561 | 560 / 562 |

-continued

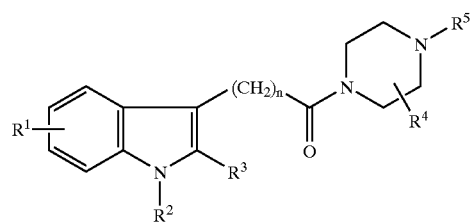

| Ex. | R¹ | R² | R³ | n | R⁴ | R⁵ | Formula | M.W. | m/z (ES⁺) (M + 1) |
|---|---|---|---|---|---|---|---|---|---|
| 12 | 5-Methyl | H | 3,5-diMe-phenyl | 2 | 1,4-dimethylpiperazine | 2-MeO-phenyl | C31H35N3O2 | 481 | 482 |
| 13 | H | Me | phenyl | 2 | 1,4-dimethylpiperazine | 2-MeO-phenyl | C29H31N3O2 | 453 | 454 |
| 14 | H | Me | 2-naphthyl | 2 | 1,4-dimethylpiperazine | 2-MeO-phenyl | C33H33N3O2 | 503 | 504 |
| 15 | H | Me | 2-naphthyl | 3 | 1,4-dimethylpiperazine | 2-MeO-phenyl | C34H35N3O2 | 517 | 518 |
| 16 | H | Me | 3-Br-phenyl | 2 | 1,4-dimethylpiperazine | 2-MeO-phenyl | C29H30BrN3O2 | 531 / 533 | 532 / 534 |
| 17 | H | Me | 4-Br-phenyl | 2 | 1,4-dimethylpiperazine | 2-MeO-phenyl | C29H30BrN3O2 | 531 / 533 | 532 / 534 |
| 18 | H | Me | 4-Br-phenyl | 3 | 1,4-dimethylpiperazine | 2-MeO-phenyl | C30H32BrN3O2 | 545 / 547 | 546 / 548 |
| 19 | H | Me | 3,5-diMe-phenyl | 2 | 1,4-dimethylpiperazine | 2-MeO-phenyl | C31H35N3O2 | 481 | 482 |

EXAMPLE 20

1-{3-[2-(4-Bromophenyl)-5-methyl-1H-indol-3-yl]-1-oxopropyl}-4-(3,5-dimethoxyphenyl)piperazine Diisopropylethylamine (32 mg) and bromoacetonitrile (145 mg) were to the resin of Description 2 (50 mg) in N-methylpyrrolidinone (1.2 mL) and the mixture was allowed to stand at room temperature for 24 h. The mixture was filtered and the resin was washed with N-methylpyrrolidinone (5 mL) and tetrahydrofuran (5 mL). A solution of 1-(3,5-dimethoxyphenyl)piperazine (5.2 mg) in tetrahydrofuran (1.6 mL) was added and the mixture was allowed to stand at room temperature for 24 h. The mixture was filtered, washing with tetrahydrofuran (0.5 mL) and the filtrate was collected. The solvent was evaporated under reduced pressure and the residue was dried in vacuo to give the title compound (6.8 mg). 1H NMR (360 MHz, DMSO-d$_6$) δ1.88–1.94 (2H, m), 2.17–2.21 (3H, m), 2.40 (3H, s), 2.68 (1H, m), 2.90 (2H, m), 3.01 (2H, m), 3.06–3.10 (2H, m), 3.70 (6H, s), 5.98 (1H, s), 6.03 (2H, s), 6.95 (1H, d, J 10 Hz), 7.25 (1H, d, J 10 Hz), 7.35 (1H, s), 7.58 (2H, d,j 10 Hz), and 7.70 (2H, d, J 10 Hz). m/z (ES$^+$) 562, 564 (M+1).

The following compounds were prepared according to the methods of Description 2 and Example 20, substituting an appropriate keto acid for 4-bromo-δ-oxobenzenepentanoic acid, an appropriate hydrazine for (4-methylphenyl)hydrazine hydrochloride and an appropriate amine for 1-(3,5-dimethoxyphenyl)piperazine.

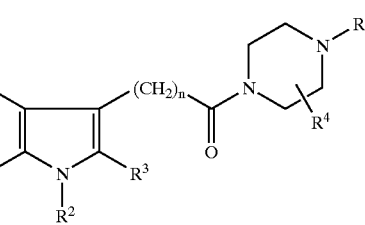

| Ex. | R$^1$ | R$^2$ | R$^3$ | n | R$^4$ | R$^5$ | Formula | M.W. | m/z (ES$^+$) (M + 1) |
|---|---|---|---|---|---|---|---|---|---|
| 21 | 5-Methyl | 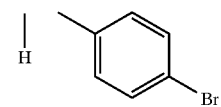 | 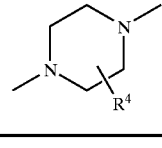 | 2 | 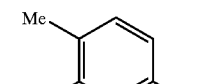 | 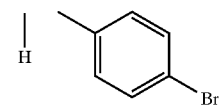 | C30H32BrN3O | 529 531 | 530 532 |
| 22 | 5-Methyl | 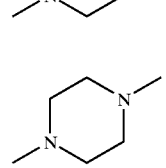 | 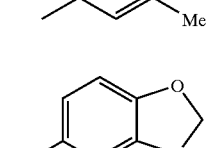 | 2 | 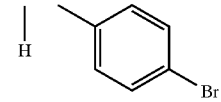 | 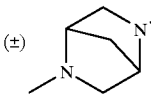 | C29H28BrN3O3 | 545 547 | 546 548 |
| 23 | 5-Methyl | 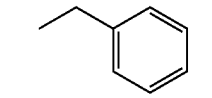 | 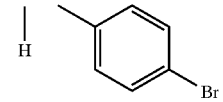 | 2 | 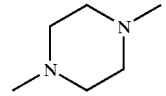 | 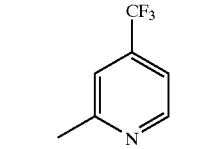 | C30H30BrN3O | 527 529 | 528 530 |
| 24 | 5-Methyl | 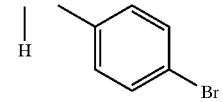 | 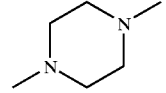 | 2 | 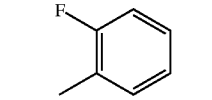 | 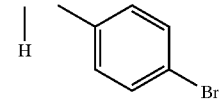 | C28H26BrF3N4O | 570 572 | 571 573 |
| 25 | 5-Methyl | 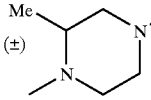 | 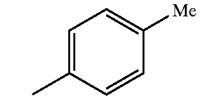 | 2 | 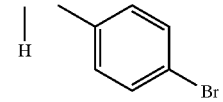 | 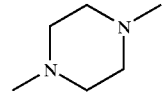 | C28H27BrFN3O | 519 521 | 520 522 |
| 26 | 5-Methyl | | | 2 | | | C30H32BrN3O | 529 531 | 530 532 |
| 27 | 5-Methyl | | | 2 | | 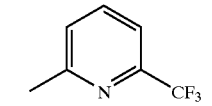 | C28H26BrF3N4O | 570 572 | 571 573 |

-continued

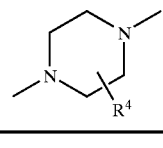

| Ex. | R¹ | R² | R³ | n | R⁴ | R⁵ | Formula | M.W. | m/z (ES⁺) (M + 1) |
|---|---|---|---|---|---|---|---|---|---|
| 28 | 5-Methyl | H | 4-Br-phenyl | 2 | N-methylpiperazine | 1-(4-chlorophenyl)ethyl (±) | C35H33BrClN3O | 625 627 | 626 628 |
| 29 | 5-Methyl | H | 4-Br-phenyl | 2 | 2,4-dimethylpiperazine (±) | 3-methylphenyl | C30H32BrN3O | 529 531 | 530 532 |
| 30 | 5-Methyl | H | 4-Br-phenyl | 2 | 2,4-dimethylpiperazine (±) | 4-methoxyphenyl | C30H32BrN3O2 | 545 547 | 546 548 |
| 31 | 5-Methyl | H | 4-Br-phenyl | 2 | N-methylpiperazine | 3-chlorophenyl | C28H27BrClN3O | 535 537 | 536 538 |
| 32 | 5-Methyl | H | 4-Br-phenyl | 2 | N-methylpiperazine | 2,3-dimethylphenyl | C30H32BrN3O | 529 531 | 530 532 |
| 33 | 5-Methyl | H | 4-Br-phenyl | 2 | N-methylpiperazine | bis(4-fluorophenyl)methyl | C35H32BrF2N3O | 627 629 | 628 630 |
| 34 | 5-Methyl | H | 4-Br-phenyl | 2 | 2,4-dimethylpiperazine (±) | 4-chlorophenyl | C29H29BrClN3O | 549 551 | 550 552 |

-continued

| Ex. | R¹ | R² | R³ | n | R⁴ | R⁵ | Formula | M.W. | m/z (ES⁺) (M + 1) |
|---|---|---|---|---|---|---|---|---|---|
| 35 | 5-Methyl | H | 4-Br-phenyl | 2 | 2,5-dimethylpiperazinyl | cyclohexyl | C28H34BrN3O | 507, 509 | 508, 510 |
| 36 | 5-Methyl | H | 4-Br-phenyl | 2 | 2,5-dimethylpiperazinyl | 2,5-dimethylphenyl (Me, Me) | C30H32BrN3O | 529, 531 | 530, 532 |
| 37 | 5-Methyl | H | 4-Br-phenyl | 2 | 2,5-dimethylpiperazinyl | 2,5-dimethoxyphenyl (MeO, OMe) | C30H32BrN3O3 | 561, 563 | 562, 564 |
| 38 | 5-Methyl | H | 4-Br-phenyl | 2 | 2,5-dimethylpiperazinyl | (±)-1-phenylethyl | C30H32BrN3O | 529, 531 | 530, 532 |
| 39 | 5-Methyl | H | 4-Br-phenyl | 2 | 2,5-dimethylpiperazinyl | 3-methylphenyl (Me) | C29H30BrN3O | 515, 517 | 516, 518 |
| 40 | 5-Methyl | H | 4-Br-phenyl | 2 | 2,5-dimethylpiperazinyl | 2-ethylphenyl (Et) | C30H32BrN3O | 529, 531 | 530, 532 |
| 41 | 5-Methyl | H | 4-Br-phenyl | 2 | 2,5-dimethylpiperazinyl | 2-methylthiophenyl (MeS) | C29H30BrN3OS | 547, 549 | 548, 550 |
| 42 | 5-Methyl | H | 4-Br-phenyl | 2 | 2,5-dimethylpiperazinyl | 2-chlorophenyl (Cl) | C28H27BrClN3O | 535, 537 | 536, 538 |
| 43 | 5-Methyl | H | 4-Br-phenyl | 2 | 2,5-dimethylpiperazinyl | but-3-enyl | C25H28BrN3O | 465, 467 | 466, 468 |
| 44 | 5-Methyl | H | 4-Br-phenyl | 2 | 2,5-dimethylpiperazinyl | 3-(diallylamino)propyl | C30H37BrN4O | 548, 550 | 549, 551 |

-continued

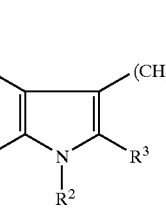

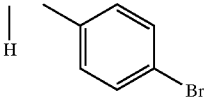

| Ex. | R¹ | R² | R³ | n | R⁴ | R⁵ | Formula | M.W. | m/z (ES⁺) (M + 1) |
|---|---|---|---|---|---|---|---|---|---|
| 45 | 5-Methyl | H | 4-Br-phenyl | 2 | N-methylpiperazine | 2-nitro-tolyl | C28H27BrN4O3 | 546 / 548 | 547 / 549 |
| 46 | 5-Methyl | H | 4-Br-phenyl | 2 | N-methylpiperazine | N-methyl-N-phenyl-propanamide | C31H33BrN4O2 | 572 / 574 | 573 / 575 |
| 47 | 5-Methyl | H | 4-Br-phenyl | 2 | N-methylpiperazine | 2,6-dimethyl-4-methoxyphenyl (substituted) | C31H34BrN3O2 | 559 / 561 | 560 / 562 |
| 48 | 5-Methyl | H | 4-Br-phenyl | 2 | N-methylpiperazine | propyl-cyclohexyl | C30H38BrN3O | 535 / 537 | 536 / 538 |
| 49 | 5-Methyl | H | 4-Br-phenyl | 2 | N-methylpiperazine | 3,4-dimethoxyphenyl-methyl | C30H32BrN3O3 | 561 / 563 | 562 / 564 |
| 50 | 5-Methyl | H | 4-Br-phenyl | 2 | N-methylpiperazine | 4-ethoxyphenyl | C30H32BrN3O2 | 545 / 547 | 546 / 548 |
| 51 | 5-Methyl | H | 4-Br-phenyl | 2 | N-methylpiperazine | 4-methylphenyl | C29H30BrN3O | 515 / 517 | 516 / 518 |
| 52 | 5-Methyl | H | 4-Br-phenyl | 2 | N-methylpiperazine | 2-methylphenyl | C29H30BrN3O | 515 / 517 | 516 / 518 |

-continued

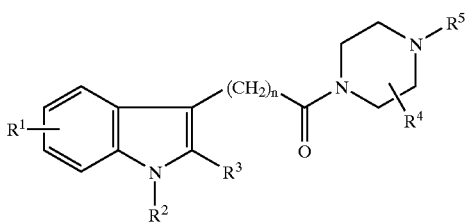

| Ex. | R[1] | R[2] | R[3] | n | R[4] | R[5] | Formula | M.W. | m/z (ES+) (M + 1) |
|---|---|---|---|---|---|---|---|---|---|
| 53 | 5-Methyl | H | 4-Br-C6H4 | 2 | N-Me piperazine | 2-CN-C6H4 | C29H27BrN4O | 526 528 | 527 529 |
| 54 | 5-Methyl | H | 4-Br-C6H4 | 2 | (±) 2-Me-N-Me piperazine | 3-Cl-C6H4 | C29H29BrClN3O | 549 551 | 550 552 |
| 55[1] | 4-Chloro 6-Chloro | H | 4-Cl-C6H4 | 2 | N-Me piperazine | 2-MeO-C6H4 | C28H27Cl2N3O2 | 507 509 | 508 510 |
| 56[1] | 4,5-Dichloro 5,6-Dichloro | H | 4-Cl-C6H4 | 2 | N-Me piperazine | 2-MeO-C6H4 | C28H26Cl3N3O2 | 541 543 | 542 544 |
| 57 | 5,7-Dichloro | H | 4-Cl-C6H4 | 2 | N-Me piperazine | 2-MeO-C6H4 | C28H26Cl3N3O2 | 541 543 | 542 544 |
| 58 | 5-Trifluoromethoxy | H | 4-Cl-C6H4 | 2 | N-Me piperazine | 2-MeO-C6H4 | C29H27ClF3N3O3 | 557 559 | 558 560 |

[1]1:1 Mixture of isomers

The following compounds were prepared from 5-chloro-2-(4-chlorophenyl)-1H-indole-3-propanoic acid (Description 11) or 5-methyl-2-phenyl-1H-indole-3-propanoic acid (Description 7) according to the methods of Description 13 and Example 20, substituting an appropriate amine for dimethoxyphenyl)piperazine.

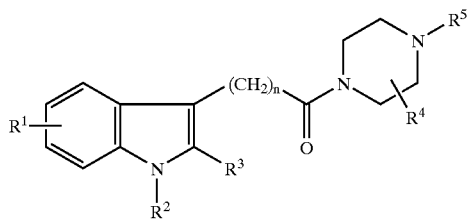

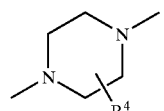

| Ex. | R¹ | R² | R³ | n | R⁴ | R⁵ | Formula | M.W. | m/z (ES⁺) (M + 1) |
|---|---|---|---|---|---|---|---|---|---|
| 59 | 5-Methyl | H | phenyl | 2 | 1,4-dimethylpiperazine | 2-Cl-phenyl | C28H28ClN3O | 457 459 | 458 460 |
| 60 | 5-Methyl | H | phenyl | 2 | 1,4-dimethylpiperazine | 2-F-phenyl | C28H28FN3O | 441 | 442 |
| 61 | 5-Methyl | H | phenyl | 2 | 1,4-dimethylpiperazine | 2-Me-phenyl | C29H31N3O | 437 | 438 |
| 62 | 5-Methyl | H | phenyl | 2 | 1,4-dimethylpiperazine | 4-OMe-phenyl | C29H31N3O2 | 453 | 454 |
| 63 | 5-Methyl | H | phenyl | 2 | 1,4-dimethylpiperazine | 2,3-diMe-phenyl | C30H33N3O | 451 | 452 |
| 64 | 5-Methyl | H | phenyl | 2 | 1,4-dimethylpiperazine | 2,4-diMe-phenyl | C30H33N3O | 451 | 452 |
| 65¹ | 5-Methyl | H | phenyl | 2 | 1,4-dimethylpiperazine | 3,5-diMe-phenyl | C30H33N3O | 451 | 452 |
| 66² | 5-Methyl | H | phenyl | 2 | 1,4-dimethylpiperazine | 4-OMe-3-Me-6-OCF3-phenyl | C30H30F3N3O3 | 537 | 538 |
| 67 | 5-Methyl | H | phenyl | 2 | 1,4-dimethylpiperazine | 3-OMe-phenyl | C29H31N3O2 | 453 | 454 |

-continued

| Ex. | R¹ | R² | R³ | n | R⁴ | R⁵ | Formula | M.W. | m/z (ES⁺) (M + 1) |
|---|---|---|---|---|---|---|---|---|---|
| 68 | 5-Methyl | H | phenyl | 2 | 1,4-dimethylpiperazine | 3-methylphenyl | C29H31N3O | 437 | 438 |
| 69 | 5-Methyl | H | phenyl | 2 | 1,4-dimethylpiperazine | 3-chlorophenyl | C28H28ClN3O | 457 459 | 458 460 |
| 70 | 5-Methyl | H | phenyl | 2 | 1,4-dimethylpiperazine | 3-(trifluoromethyl)phenyl | C29H28F3N3O | 491 | 492 |
| 71 | 5-Chloro | H | 4-chlorophenyl | 2 | 1,4-dimethylpiperazine | phenyl | C28H27Cl2N3O | 491 493 | 492 494 |
| 72¹ | 5-Chloro | H | 4-chlorophenyl | 2 | 1,4-dimethylpiperazine | 3,5-dimethylphenyl | C29H29Cl2N3O | 505 507 | 506 508 |
| 73 | 5-Chloro | H | 4-chlorophenyl | 2 | 1,4-dimethylpiperazine | 2,4-difluorophenyl | C27H23Cl2F2N3O | 513 515 | 514 516 |
| 74 | 5-Chloro | H | 4-chlorophenyl | 2 | 1,4-dimethylpiperazine | benzo[1,3]dioxol-5-ylmethyl | C29H27Cl2N3O3 | 535 537 | 536 538 |
| 75 | 5-Chloro | H | 4-chlorophenyl | 2 | 1,4-dimethylpiperazine | cinnamyl | C30H29Cl2N3O | 517 519 | 518 520 |

-continued

| Ex. | R¹ | R² | R³ | n | R⁴ | R⁵ | Formula | M.W. | m/z (ES⁺) (M + 1) |
|---|---|---|---|---|---|---|---|---|---|
| 76 | 5-Chloro | H | 4-chlorophenyl | 2 | 4-methylpiperazin-1-yl | 3-methoxyphenyl (OMe) | C28H27Cl2N3O2 | 507 509 | 508 510 |
| 77[3] | 5-Chloro | H | 4-chlorophenyl | 2 | 4-methylpiperazin-1-yl | 3-ethoxyphenyl (OEt) | C29H29Cl2N3O2 | 521 523 | 522 524 |
| 78[4] | 5-Chloro | H | 4-chlorophenyl | 2 | 4-methylpiperazin-1-yl | 3-isopropoxyphenyl (OiPr) | C30H31Cl2N3O2 | 535 537 | 536 538 |

[1] 1-(3,5-Dimethylphenyl)piperazine; Bull Soc Chim Fr. 1987, 1, 205–211.
[2] 1-[2-Methoxy-4-(trifluoromethoxy)phenyl]piperazine; Description 18
[3] 1-(3-Ethoxyphenyl)piperazine; Description 22.
[4] 1-[3-(1-Methylethoxy)phenyl]piperazine; Description 23.

EXAMPLE 79

1-{3-[5-Chloro-2-(4-chlorophenyl)-1-methyl-1H-indol-3-yl]-1-oxopropyl}-4-(phenylmethyl)piperazine 1,1-Carbonyl diimidazole (47 mg, 0.29 mmol) was added to a solution of 5-chloro-2-(4-chlorophenyl)-1-methyl-1H-indole-3-propanoic acid (Description 12, 100 mg, 0.29 mmol) in tetrahydrofuran (4 mL) and the mixture was heated under reflux for 2 h. The mixture was cooled and 1-(phenylmethyl)piperazine (48 mg, 0.27 mmol) was added. The mixture was stirred at room temperature overnight and the solvent was evaporated under reduced pressure. Water (4 mL) was added and the mixture was stirred at 80° C. for 2 h. The mixture was cooled, the water was decanted and the residue was dissolved in dichloromethane. Using a Bond Elut™ cartridge to separate the layers the solution was washed with hydrochloric acid (1M), and aqueous sodium hydroxide (2M). The organic fraction was evaporated under reduced pressure to a small volume and filtered through a plug of silica on a Bond Elut™ cartridge, eluting with hexane/EtOAc (85:15 increasing to 70:30), to give the title compound as a colorless solid (95 mg, 65%). $^1$H NMR (360 MHz, CDCl$_3$) δ2.10–2.13 (2H, m), 2.25–2.28 (2H, m), 2.40–2.43 (2H, m), 2.89–2.93 (2H, m), 3.13–3.16 (2H, m), 3.78 (2H, s), 3.46 (3H, s), 3.48–3.51 (2H, m), 7.10–7.26 (9H, m), 7.40 (2H, d, J 8.3 Hz), and 7.50 (1H, s). m/z (ES⁺) 506, 508 (M+1).

EXAMPLE 80

1.1-Dimethylethyl 4-{3-[5-Chloro-2-(4-chlorophenyl)-1H-indol-3-yl]-1-oxopropyl}-1-piperazinecarboxylate Prepared from 5-chloro-2-(4-chlorophenyl)-1H-indole-3-propanoic acid (Description 11) and 1,1-dimethylethyl 1-piperazinecarboxylate according to the method of Example 79. $^1$H NMR (360 MHz, CDCl$_3$) δ1.45 (9H, s), 2.60–2.65 (2H, m), 3.19–3.24 (6H, m), 3.30–3.33 (2H, m), 3.53–3.57 (2H, m), 7.16 (1H, dd, J 8.6, 1.8 Hz), 7.26 (1H, d, J 8.6 Hz), 7.43–7.50 (4H, m), 7.56(1H, d, J 1.8 Hz), and 8.08 (1H, s).

The following compounds were prepared according to the method of Example 79, substituting an appropriate acid for 5-chloro-2-(4-chlorophenyl)-1-methyl-1H-indole-3-propanoic acid and an appropriate amine, or amine hydrochloride for 1-(phenylmethyl)piperazine. If an amine hydrochloride was used, triethylamine (1 eq.) was added to the reaction mixture. If the product contained a strongly basic group, the hydrochloric acid wash was omitted.

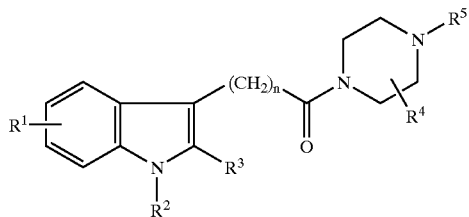

| Ex. | R¹ | R² | R³ | n | R⁴ | R⁵ | Formula | M.W. | m/z (ES⁺) (M + 1) |
|---|---|---|---|---|---|---|---|---|---|
| 81 | 5-Methyl | H | phenyl | 1 | 1,4-dimethylpiperazine | 2-MeO-phenyl | C28H29N3O2 | 439 | 440 |
| 82 | 5-Chloro | H | phenyl | 2 | 1,4-dimethylpiperazine | 2-MeO-phenyl | C28H28ClN3O2 | 473, 475 | 474, 476 |
| 83 | 5-Fluoro | H | phenyl | 2 | 1,4-dimethylpiperazine | 2-MeO-phenyl | C28H28FN3O2 | 457 | 458 |
| 84[1] | 5,6-Dimethyl 4,5-Dimethyl | H | phenyl | 2 | 1,4-dimethylpiperazine | 2-MeO-phenyl | C30H33N3O2 | 467 | 468 |
| 85 | 5-Chloro | H | 4-Cl-phenyl | 2 | 1,4-dimethylpiperazine | 2-MeO-phenyl | C28H27Cl2N3O2 | 507, 509 | 508, 510 |
| 86 | 5-Chloro | Me | 4-Cl-phenyl | 2 | 1,4-dimethylpiperazine | 4-methylnaphthyl | C32H29Cl2N3O | 541, 543 | 542, 544 |
| 87 | 5-Chloro | Me | 4-Cl-phenyl | 2 | 1,4-dimethylpiperazine | cyclohexyl | C28H33Cl2N3O | 497, 499 | 598, 500 |
| 88 | 5-Chloro | Me | 4-Cl-phenyl | 2 | 1,4-dimethylpiperazine | n-propyl | C25H29Cl2N3O | 457, 459 | 458, 460 |
| 89 | 5-Chloro | Me | 4-Cl-phenyl | 2 | 1,4-dimethylpiperazine | isopropyl | C25H29Cl2N3O | 457, 459 | 458, 460 |

-continued

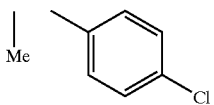

| Ex. | R¹ | R² | R³ | n | R⁴ | R⁵ | Formula | M.W. | m/z (ES⁺) (M + 1) |
|---|---|---|---|---|---|---|---|---|---|
| 90 | 5-Chloro | Me | 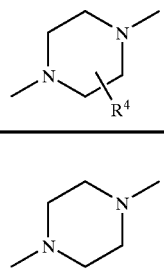 | 2 | 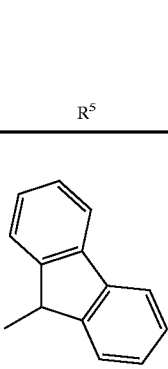 | 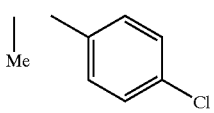 | C35H31Cl2N3O | 579<br>581 | 580<br>582 |
| 91 | 5-Chloro | Me | 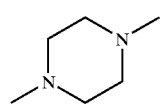 | 2 | 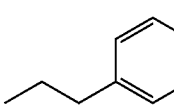 | 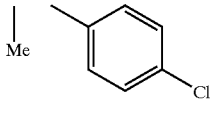 | C30H31Cl2N3O | 519<br>521 | 520<br>522 |
| 92² | 5-Chloro | Me | 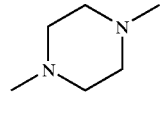 | 2 | 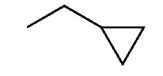 | 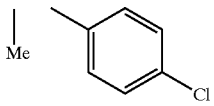 | C26H29Cl2N3O | 469<br>471 | 470<br>472 |
| 93³ | 5-Chloro | Me | 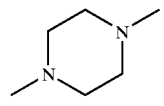 | 2 | 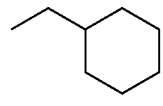 | 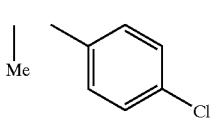 | C29H35Cl2N3O | 511<br>513 | 512<br>514 |
| 94 | 5-Chloro | Me | 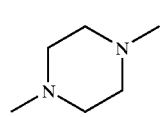 | 2 | 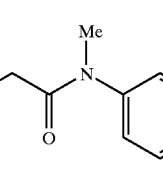 | 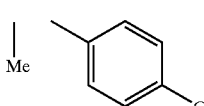 | C31H32Cl2N4O2 | 562<br>564 | 563<br>565 |
| 95 | 5-Chloro | Me | 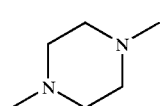 | 2 | 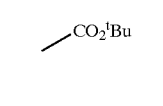 | CO₂ᵗBu | C27H31Cl2N3O3 | 515<br>517 | 516<br>518 |
| 96 | 5-Chloro | Me | 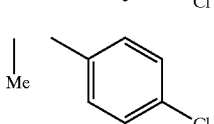 | 2 | 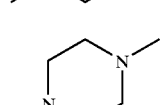 | 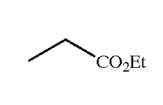 CO₂Et | C26H29Cl2N3O3 | 501<br>503 | 502<br>504 |

¹2:1 Mixture of isomers.
²1-(Cyclopropylmethyl)piperazine; J. Med. Chem. 1996, 39, 2068–2080.
³1-(Cyclohexylmethyl)piperazine; J. Med. Chem. 1992, 35, 2688–2696.

EXAMPLE 97

1-{3-[5-Chloro-2-(4-chlorophenyl)-1-methyl-1H-indol-3-yl]-1-oxopropyl}-4-[2-(trifluoromethoxy)phenyl]piperazine Prepared from 5-chloro-2-(4-chlorophenyl)-1-methyl-1H-indole-3-propanoic acid (Description 12) and 1-[2-(trifluoromethoxy)phenyl]piperazine hydrochloride (Description 19) according to the method of Description 25. ¹H NMR (360 MHz, CDCl₃) δ7.60 (1H, d, J 1.7 Hz), 7.49 (2H, m), 7.32 (2H, m), 7.24–7.18 (4H, m), 7.04–7.00 (1H, m), 6.93 (1H, dd, J 1.3, 8.0 Hz), 3.71 (2H, t, J 5.0 Hz), 3.54 (3H, s), 3.37 (2H, t, J 5.0 Hz), 3.02 (2H, m), 2.95 (2H, t, J 5.0 Hz), 2.80 (2H, t, J 5.0 Hz), and 2.54 (2H, m). m/z (ES⁺) 576, 578 (M+1).

EXAMPLE 98

4-{[3,5-Bis(trifluoromethyl)phenyl]methyl}-1-{3-[5-chloro-2-(4-chlorophenyl)-1H-indol-3-yl]-1-oxopropyl}piperazine 1-(Bromomethyl)-3,5-bis(trifluoromethyl)benzene (83 mg) was added to a mixture of 1-{3-[5-chloro-2-(4-chlorophenyl)-1H-indol-3-yl]-1-oxopropyl}piperazine (Description 30, 35 mg) and potassium carbonate (36 mg) in acetone (3 mL) and the mixture was stirred at room temperature for 2 h. Methanol (1 mL) and ethyl acetate (10 mL) were added and the mixture was washed with water. The organic fraction was filtered through a plug of silica in a Bond Elut™ cartridge, eluting with hexane/EtOAc (80:20 increasing to 60:40), to give the title compound as a colorless solid (49 mg, 89%). $^1$H NMR (360 MHz, CDCl$_3$) δ2.16–2.19 (2H, m), 2.33–2.36 (2H, m), 2.59–2.63 (2H, m), 3.15–3.20 (2H, m), 3.28–3.30 (2H, m), 3.53 (2H, s), 3.58–3.61 (2H, m), 7.13 (1H, dd, J 8.7, 1.8 Hz), 7.25 (1H, d, J 8.3 Hz), 7.36–7.53 (6H, m), 7.77 (2H, s), and 8.51 (1H, s). m/z (ES$^+$) 628, 630 (M+1).

The following compounds were prepared from 1-{3-[5-chloro-2-(4-chlorophenyl)-1H-indol-3-yl]-1-oxopropyl}piperazine (Description 30) or 1-{3-[5-chloro-2-(4-chlorophenyl)-1-methyl-1H-indol-3-yl]-1-oxopropyl}piperazine (Description 31) according to the method of Example 98, substituting an appropriate alkyl bromide or chloride for 1-(bromomethyl)-3,5-bis(trifluoromethyl)benzene.

| Ex. | R$^1$ | R$^2$ | R$^3$ | n | R$^4$ | R$^5$ | Formula | M.W. | m/z (ES$^+$) (M + 1) |
|---|---|---|---|---|---|---|---|---|---|
| 99 | 5-Chloro | H | 4-chlorophenyl | 2 | dimethylpiperazine | 2-OMe-benzyl | C29H29Cl2N3O2 | 521 / 523 | 522 / 524 |
| 100 | 5-Chloro | H | 4-chlorophenyl | 2 | dimethylpiperazine | 3-OMe-benzyl | C29H29Cl2N3O2 | 521 / 523 | 522 / 524 |
| 101 | 5-Chloro | H | 4-chlorophenyl | 2 | dimethylpiperazine | 2-Cl-benzyl | C28H26Cl3N3O | 525 / 527 | 526 / 528 |
| 102 | 5-Chloro | H | 4-chlorophenyl | 2 | dimethylpiperazine | 4-Cl-benzyl | C28H26Cl3N3O | 525 / 527 | 526 / 528 |
| 103 | 5-Chloro | H | 4-chlorophenyl | 2 | dimethylpiperazine | 4-F-benzyl | C28H26Cl2FN3O | 509 / 511 | 510 |
| 104 | 5-Chloro | H | 4-chlorophenyl | 2 | dimethylpiperazine | 2-NO$_2$-benzyl | C28H26Cl2N4O3 | 536 / 538 | 537 / 539 |

US 6,518,273 B1

-continued

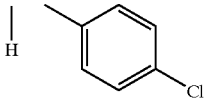

| Ex. | R¹ | R² | R³ | n | R⁴ | R⁵ | Formula | M.W. | m/z (ES⁺) (M + 1) |
|---|---|---|---|---|---|---|---|---|---|
| 105 | 5-Chloro | H | 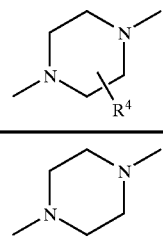 | 2 | 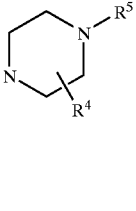 | 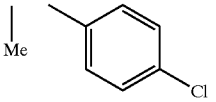 NO₂ | C28H26Cl2N4O3 | 536 538 | 537 539 |
| 106 | 5-Chloro | Me |  | 2 | 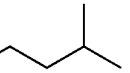 | 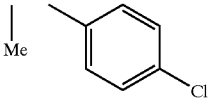 | C27H33Cl2N3O | 485 487 | 486 488 |
| 107[1] | 5-Chloro | Me |  | 2 | 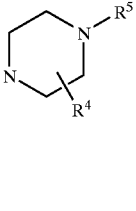 | 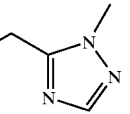 | C26H28Cl2N6O | 510 512 | 511 513 |

[1] 5-Chloromethyl-1-methyl-1,2,4-triazole hydrochloride; EP-170073.

EXAMPLE 108

4-Benzoyl-1-{3-[5-chloro-2-(4-chlorophenyl)-1H-indol-3-yl]-1-oxopropyl}piperazine Benzoyl chloride (0.011 mL) was added to a stirred solution of 1-{3-[5-chloro-2-(4-chlorophenyl)-1H -indol-3-yl]-1-oxopropyl}piperazine (Description 30, 35 mg) in pyridine (0.5 mL) and the mixture was stirred at room temperature for 3 h. The solvent was evaporated under reduced pressure, hydrochloric acid (2M, 5 mL) and ethyl acetate (5 mL) were added and the layers were separated. The organic layer was dried (MgSO₄) and the solvent was evaporated under reduced pressure. The residue was crystallized from dichloromethane/ethyl acetate (4:1) to give the title compound as a colorless solid (25 mg, 58%). ¹H NMR (360 MHz, CDCl₃) δ2.56–2.68 (2H, m), 3.02–3.67 (10H, m), 7.17 (1H, dd, J 8.6, 1.8 Hz), 7.28 (1H, d, J 8.6 Hz), 7.33–7.50 (9H, m), 7.56 (1H, s), and 8.13 (1H, s). m/z (ES⁺) 506, 508 (M+1).

EXAMPLE 109

Ethyl 4-{3-[5-Chloro-2-(4-chlorophenyl)-1H-indol-3-yl]-1-oxopropyl}piperazine-1-acetate Prepared from 5-chloro-2-(4-chlorophenyl)-1H-indole-3-propanoic acid (Description 11) and ethyl 1-piperazinecarboxylate according to the method of Example 79. ¹H NMR (250 MHz, CDCl₃) δ1.26 (3H, t, J 7.3 Hz), 2.34 (2H, t, J 4.8 Hz), 2.48 (2H, t, J 5.3 Hz), 2.62 (2H, t, J 7.8 Hz), 3.16 (2H, s), 3.18–3.23 (2H, m), 3.29–3.35 (2H, m), 3.64 (2E, t, J 5.0 Hz), 4.17 (2H, dd, J 14.0, 7.3 Hz), 7.16 (1H, dd, J 8.5, 1.8 Hz), 7.28 (1H, d, J 8.8 Hz), 7.42–7.50 (4H, m), 7.56 (1H, d, J 1.8 Hz), and 8.13 (1H, s).

EXAMPLE 110

4-{3-[5-Chloro-2-(4-chlorophenyl)-1H-indol-3-yl]-1-oxopropyl}piperazine-1-acetic Acid Potassium hydroxide (320 mg) was added to a solution of ethyl 4-{3-[5-chloro-2-(4-chlorophenyl)-1H-indol-3-yl]-1-oxopropyl}piperazine-1-acetate (Example 109, 350 mg, 0.72 mmol) in methanol and the mixture was stirred at room temperature overnight. Water was added and the pH was adjusted to 7.0 with hydrochloric acid (2M). The mixture was extracted with ethyl acetate, the combined organic fractions were dried (MgSO₄) and the solvent was evaporated under reduced pressure. The residue was crystallised from ethyl acetate:methanol (99:1) to give the title compound as a pale solid (300 mg, 90%). ¹H NMR (250 MHz, CD₃OD) δ2.20–2.26 (2H, m), 2.92–2.97 (2H, m), 3.10–3.25 (4H, m), 3.55–3.60 (2H, m), 3.90–4.01 (4H, m), 7.10 (1H, dd, J 8.8, 2.0 Hz), 7.38 (1H, d, J 8.8 Hz), and 7.45–7.60 (5H, m). m/z (ES⁺) 460, 462 (M+1).

The following compounds were prepared from 4-{3-[5-chloro-2-(4-chlorophenyl)-1H-indol-3-yl]-1-oxopropyl}piperazine-1-acetic acid (Example 110) according to the method of Example 79, substituting an appropriate amine for 1-(phenylmethyl)piperazine.

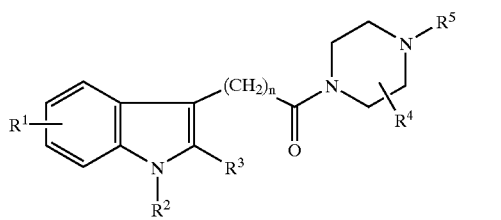

| Ex. | R¹ | R² | R³ | n | R⁴ | R⁵ | Formula | M.W. | m/z (ES⁺) (M + 1) |
|---|---|---|---|---|---|---|---|---|---|
| 111 | 5-Chloro | H | 4-Cl-C₆H₄ | 2 | N-methylpiperazinyl | -CH₂CH₂C(O)NH-CH₂-Ph | C30H30Cl2N4O2 | 548 550 | 549 551 |
| 112 | 5-Chloro | H | 4-Cl-C₆H₄ | 2 | N-methylpiperazinyl | -CH₂CH₂C(O)N(Me)-CH₂-Ph | C30H30Cl2N4O2 | 548 550 | 549 551 |
| 113 | 5-Chloro | H | 4-Cl-C₆H₄ | 2 | N-methylpiperazinyl | -CH₂CH₂C(O)N(Me)-allyl | C27H30Cl2N4O2 | 512 514 | 513 515 |
| 114 | 5-Chloro | H | 4-Cl-C₆H₄ | 2 | N-methylpiperazinyl | -CH₂CH₂C(O)-indolinyl | C31H30Cl2N4O2 | 560 562 | 561 563 |
| 115 | 5-Chloro | H | 4-Cl-C₆H₄ | 2 | N-methylpiperazinyl | -CH₂C(O)NH-Ph | C29H28Cl2N4O2 | 534 536 | 535 537 |
| 116 | 5-Chloro | H | 4-Cl-C₆H₄ | 2 | N-methylpiperazinyl | -CH₂CH₂C(O)-tetrahydroisoquinolinyl | C32H32Cl2N4O2 | 574 576 | 575 577 |

EXAMPLE 117

4-(2-Methoxyphenyl)-1-{3-[5-methyl-2-(4-methylphenyl)-1H-indol-3-yl]-1-oxopropyl}piperazine Hydrochloride Aqueous sodium carbonate (2M, 3 mL) was added to a solution of 1-[3-(2-bromo-5-methyl-1H-indol-3-yl)-1-oxopropyl]-4-(2-methoxyphenyl)piperazine (Description 28, 70 mg, 0.15 mmol) and (4-methylphenyl)boronic acid (42 mg, 0.3 mmol) in DME (10 mL) and the mixture was degassed with bubbling nitrogen. [1,4-Butanediylbis(diphenylphosphine-κP)] dichloropalladium (*Organometallics* 1998, 17, 661; 10 mg) was added and the mixture was degassed and stirred at 85° C. for 18 h. The reaction mixture was cooled, poured into water and extracted with ethyl acetate. The combined organic fractions were dried (MgSO₄), the solvent was evaporated under reduced pressure and the residue was purified by flash column chromatography on silica gel, eluting with hexane/EtOAc (35:65). The residue was dissolved in ethyl acetate and ethereal hydrogen chloride (1M, 0.5 mL) was added. The solid was collected and dried in vacuo to give the title compound as a colorless solid (30 mg, 40%). ¹H NMR (360 MHz, DMSO-d₆) δ10.79 (1H, br s), 7.32 (2H, d, J 8.1 Hz), 7.11 (3H, m), 7.03 (1H, d, J 8.1 Hz), 6.92–6.85 (3H, m), 6.77–6.70 (2H, m), 3.61 (3H, s), 3.47 (2H, m), 3.33 (2H, m), 2.88 (2H, mn), 2.79 (2H, m), 2.70 (2H, m), 2.48 (2H, m), 2.19 (3H, s), and 2.16 (3H, s). m/z (ES+) 468 (M+1).

The following compounds were prepared from 1-[3-(2-bromo-1H-indol-3-yl)-1-oxopropyl]-4-(2-methoxyphenyl)piperazine (Description 27) or 1-[3-(2-bromo-5-methyl-1H-indol-3-yl)-1-oxopropyl]-4-(2methoxyphenyl)piperazine (Description 28) and an appropriately substituted phenylboronic acid according to the method of Example 117.

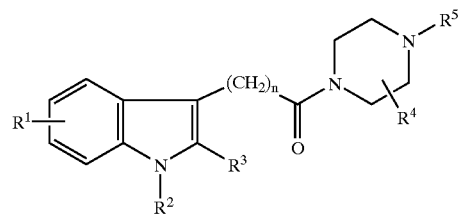

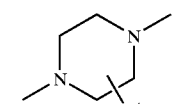

| Ex. | $R^1$ | $R^2$ | $R^3$ | n | $R^4$ | $R^5$ | Formula | M.W. | m/z (ES+) (M + 1) |
|---|---|---|---|---|---|---|---|---|---|
| 118 | H | H | 4-Cl-phenyl | 2 | | 2-MeO-phenyl | C28H28ClN3O2 | 473 475 | 474 476 |
| 119 | 5-Methyl | H | 4-Cl-phenyl | 2 | | 2-MeO-phenyl | C29H30ClN3O2 | 487 489 | 488 490 |
| 120 | 5-Methyl | H | 4-OMe-phenyl | 2 | | 2-MeO-phenyl | C30H33N3O3 | 483 | 484 |
| 121 | 5-Methyl | H | 3-Cl-phenyl | 2 | | 2-MeO-phenyl | C29H30ClN3O2 | 487 489 | 488 490 |
| 122 | 5-Methyl | H | 3-OMe-phenyl | 2 | | 2-MeO-phenyl | C30H33N3O3 | 483 | 484 |
| 123 | 5-Methyl | H | 2-OMe-phenyl | 2 | | 2-MeO-phenyl | C30H33N3O3 | 483 | 484 |
| 124[1] | 5-Methyl | H | 2-OMe-4-OCF3-phenyl | 2 | | 2-MeO-phenyl | C31H32F3N3O4 | 567 | 568 |

-continued

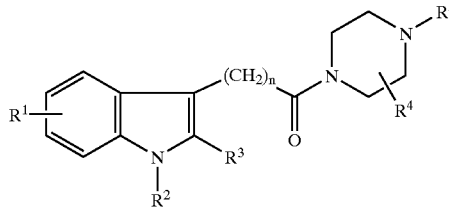

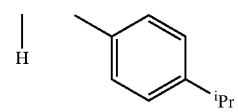

| Ex. | R¹ | R² | R³ | n | R⁴ | R⁵ | Formula | M.W. | m/z (ES⁺) (M + 1) |
|---|---|---|---|---|---|---|---|---|---|
| 125 | 5-Methyl | 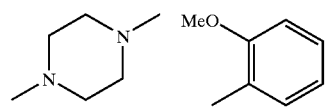 | 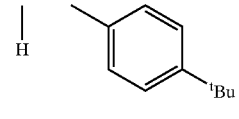 | 2 | | | C32H37N3O2 | 495 | 496 |
| 126 | 5-Methyl | 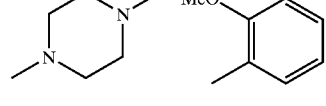 | | 2 | | | C33H39N3O2 | 509 | 510 |
| 127 | 5-Methyl | 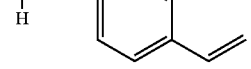 | | 2 | | | C31H33N3O2 | 479 | 480 |
| 128 | 5-Methyl |  | | 2 | | | C30H30F3N3O2 | 521 | 522 |

¹[2-Methoxy-5-(trifluoromethoxy)phenyl]boronic Acid; Description 29.

EXAMPLE 129

4-(2-Methoxyphenyl)-1-{3-[5-methyl-2-(4-phenylphenyl)-1H-indol-3-yl]-1-oxopropyl}piperazine Prepared from 1-{3-[2-(4-bromophenyl)-5-methyl-1H-indol-3-yl]-1-oxopropyl}-4-(2-methoxyphenyl)piperazine (Example 1) and phenylboronic acid according to the method of Example 117. ¹H NMR (360 MHz, CDCl₃) δ8.05 (1H, br s), 7.71–7.61 (6H, m), 7.48–7.44 (3H, m), 7.39–7.35 (1H, m), 7.29–7.25 (1H, m), 7.06–6.98 (2H, m), 6.90–6.77 (3H, m), 3.82 (3H, s), 3.78 (2H, t, J 5.0 Hz), 3.46 (2H, t, J 5.0 Hz), 3.33 (2H, m), 2.92 (2H, t, J 5.0 Hz), 2.74 (4H, m), and 2.48 (3H, s). m/z (ES⁺) 530 (M+1).

EXAMPLE 130

1-{3-[2-(4-Chlorophenyl)-1,5-dimethyl-1H-indol-3-yl]-1-oxopropyl}-4-(2-methoxyphenyl)piperazine Sodium hydride (60% dispersion in mineral oil, 2.5 mg, 0.062 mmol) was added to a solution of 1-{3-[2-(4-chlorophenyl)-5-methyl-1H-indol-3-yl]-1-oxopropyl}-4-(2-methoxyphenyl)piperazine (Example 119, 20 mg, 0.041 mmol) in N,N-dimethylformamide (1 mL) and the mixture was stirred at room temperature for 10 min. Iodomethane (5 μl, 0.12 mmol) was added and the mixture was stirred at room temperature for 10 min. Water (25 mL) was added and the mixture was extracted with ethyl acetate. The combined organic fractions were dried (MgSO₄), the solvent was evaporated under reduced pressure and the residue was purified by flash column chromatography on silica gel, eluting with hexane/ether (35:65) to give the title compound as a pale yellow foam (20 mg, 97%). ¹H NMR (360 MHz, CDCl₃) δ7.48–7.43 (3H, m), 7.33–7.31 (2H, m), 7.24–7.21 (1H, m), 7.11–7.02 (2H, m), 6.91–6.84 (3H, m), 3.86 (3H, s), 3.76 (2H, m), 3.53 (3H, s), 3.38 (2H, m), 3.04 (2H, m), 2.94 (2H, m), 2.77 (2H, m), 2.57 (2H, m), and 2.49 (3H, s). m/z (ES⁺) 502, 504 (M+1).

The following compounds were prepared according to the method of Example 130, substituting an appropriate 1H-indole for 1-{3-[2-(4-chlorophenyl)-5-methyl-1H-indol-3-yl]-1-oxopropyl}-4-(2-methoxyphenyl)piperazine and acetyl chloride, 2-bromopropane, benzyl bromide, or (2,2,2-trifluoroethyl)trichloromethanesulfonate for iodomethane.

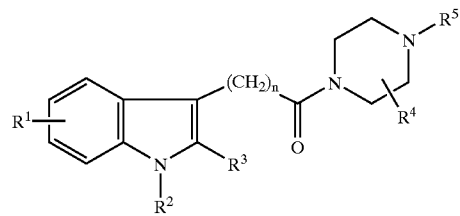

| Ex. | R¹ | R² | R³ | n | R⁴ | R⁵ | Formula | M.W. | m/z (ES⁺) (M + 1) |
|---|---|---|---|---|---|---|---|---|---|
| 131[1] | 5-Methyl | Me | 4-iPr-phenyl | 2 | (1,4-dimethylpiperazin-2-yl) | 2-MeO-phenyl | C33H39N3O2 | 509 | 510 |
| 132[2] | 5-Methyl | Me | 4-tBu-phenyl | 2 | (1,4-dimethylpiperazin-2-yl) | 2-MeO-phenyl | C34H41N3O2 | 523 | 524 |
| 133[3] | 5-Methyl | Me | 4-CF3-phenyl | 2 | (1,4-dimethylpiperazin-2-yl) | 2-MeO-phenyl | C31H32F3N3O2 | 535 | 536 |
| 134[4] | 5-Methyl | Me | 4-Br-phenyl | 2 | (1,4-dimethylpiperazin-2-yl) | 2-MeO-phenyl | C30H32BrN3O2 | 545, 547 | 546, 548 |
| 135[4] | 5-Methyl | C(O)Me | 4-Br-phenyl | 2 | (1,4-dimethylpiperazin-2-yl) | 2-MeO-phenyl | C31H32BrN3O3 | 573, 575 | 574, 576 |
| 136[5] | 5-Chloro | iPr | 4-Cl-phenyl | 2 | (1,4-dimethylpiperazin-2-yl) | 2-MeO-phenyl | C31H33Cl2N3O2 | 549, 551 | 550, 552 |
| 137[5] | 5-Chloro | CH2Ph | 4-Cl-phenyl | 2 | (1,4-dimethylpiperazin-2-yl) | 2-MeO-phenyl | C35H33Cl2N3O2 | 597, 599 | 598, 600 |
| 138[5] | 5-Chloro | CH2CF3 | 4-Cl-phenyl | 2 | (1,4-dimethylpiperazin-2-yl) | 2-MeO-phenyl | C30H28Cl2F3N3O2 | 589, 591 | 590, 592 |
| 139[5] | 5-Chloro | C(O)Me | 4-Cl-phenyl | 2 | (1,4-dimethylpiperazin-2-yl) | CH2Ph | C30H29Cl2N3O2 | 533, 535 | 534, 536 |

[1] 1-(3-{5-Methyl-2-[4-(1-methylethyl)phenyl]-1H-indol-3-yl}-1-oxopropyl)-4-(2-methoxyphenyl)piperazine; Example 125.
[2] 1-(3-{2-[4-(1,1-Dimethylethyl)phenyl]-5-methyl-1H-indol-3-yl}-1-oxopropyl)-4-(2-methoxyphenyl)piperazine; Example 126.
[3] 1-(3-{5-Methyl-2-[4-(trifluoromethyl)phenyl]-1H-indol-3-yl}-1-oxopropyl)-4-(2-methoxyphenyl)piperazine; Example 128.
[4] 1-{3-[2-(4-Bromophenyl)-5-methyl-1H-indol-3-yl]-1-oxopropyl}-4-(2-methoxyphenyl)piperazine; Example 1.
[5] 1-{3-[5-Chloro-2-(4-chlorophenyl)-1H-indol-3-yl]-1-oxopropyl}-4-(2-methoxyphenyl)piperazine; Example 85.

EXAMPLE 140

Methyl 5-Chloro-2-(4-chlorophenyl)-3-{3-[4-(2-methoxyphenyl)piperazin-1-yl]-3-oxoprop-1-yl}-1H-indole-1-acetate and 5-Chloro-2-(4-chlorophenyl)-3-{3-[4-(2-methoxyphenyl)piperazin-1-yl]-3-oxoprop-1-yl}-1H-indole-1-acetic Acid Hydrochloride Sodium hydride (60% dispersion in mineral oil, 35 mg) was added to a solution of 1-{3-[5-chloro-2-(4-chlorophenyl)-1-indol-3-yl]-1-oxopropyl}-4-(2-methoxyphenyl)piperazine (Example 85, 149 mg) in N,N-dimethylformamide (3 mL) and the mixture was stirred at room temperature for 5 min. Methyl bromoacetate (58 mg) was added and the mixture was stirred at room temperature for 5 min. Water (25 mL) was added and the mixture was extracted with ethyl acetate (25 mL). The organic fraction was washed with water (25 mL) dried ($Na_2SO_4$), the solvent was evaporated under reduced pressure and the residue was purified by flash column chromatography on silica gel, eluting with hexane/EtOAc (50:50) then with EtOAc/AcOH (99:1). The first product to elute was crystallized from hexane/EtOAc and the solid was collected and dried in vacuo to give methyl 5-chloro-2-(4-chlorophenyl)-3-{3-[4-(2-methoxyphenyl)piperazin-1-yl]-3-oxoprop-1-yl}-1H-indole-1-acetate (22 mg). m/z ($ES^+$) 580, 582 (M+1). The second product to elute was dissolved in ethanol (2 mL) and ethereal hydrogen chloride (1M, 100 μl) was added. The solvent was evaporated under reduced pressure and the residue was crystallized from hexane/EtOAc. The solid was collected and dried in vacuo to give 5-chloro-2-(4-chlorophenyl)-3-{3-[4-(2-methoxyphenyl)piperazin-1-yl]-3-oxoprop-1-yl)-}-1H-indole-1-acetic acid hydrochloride (34 mg). m/z ($ES^+$) 566, 568 (M+1).

EXAMPLE 141

5-Chloro-2-(4-chlorophenyl)-3-{3-[4-(2-methoxyphenyl)piperazin-1-yl]-3-oxoprop-1-yl}-1H-indole-1-ethanol Lithium borohydride (5 mg) was added in one portion to a solution of methyl 5-chloro-2-(4-chlorophenyl)-3-{3-[4-(2-methoxyphenyl)piperazin-1-yl]-3-oxoprop-1-yl}-1H-indole-1-acetate (Example 140, 43 mg) in THF (2 mL) and toluene (1 mL) and the mixture was stirred at room temperature for 15 min., then at 60° C. for 45 min. The mixture was cooled, hydrochloric acid (1M, 2 mL) was added and the mixture was stirred at room temperature for 10 min. Potassium carbonate and ethyl acetate (30 mL) were added and the layers were separated. The organic phase was dried ($Na_2SO_4$) and the solvent was evaporated under reduced pressure. The residue was recrystallised from ethyl acetate and the solid was collected and dried in vacuo to give the title compound as a colorless solid (21 mg). m/z ($ES^+$) 552, 554 (M+1).

EXAMPLE 142

Phenylmethyl 4-{3-[5-Chloro-2-(4-chlorophenyl)-1-methyl-1H-indol-3-yl]-1-oxopropyl}-3-oxo-1-piperazinecarboxylate Oxalyl chloride (0.08 mL, 114 mg, 0.9 mmol) was added dropwise to a stirred, cooled (0° C.) solution of 5-chloro-2-(4-chlorophenyl)-1-methyl-1H-indole-3-propanoic acid (Description 12, 330 mg, 0.95 mmol) and DMF (1 drop) in toluene (15 mL) and the mixture was stirred at room temperature for 2 h. to give a solution of 5-chloro-2-(4-chlorophenyl)-1-methyl-1H-indole-3-propanoyl chloride. Sodium hydride (60% dispersion in mineral oil, 19 mg, 0.48 mmol) was added to a solution of phenylmethyl 3-oxo-1-piperazinecarboxylate (*Eur.J.Med.Chem.* 1981, 16, 229–232) (111 mg, 0.48 mmol) in DMF (3 mL) and the mixture was stirred at room temperature for 30 min. A portion of the solution of 5-chloro-2-(4-chlorophenyl)-1-methyl-1H-indole-3-propanoyl chloride (7.5 mL) was added dropwise and the mixture was stirred at room temperature overnight. Water was added and the mixture was extracted with ether. The combined organic fractions were dried ($MgSO_4$) and the solvent was evaporated under reduced pressure. The residue was purified by flash column chromatography on silica gel, eluting with hexane/EtOAc (80:20). The fractions containing product were combined, washed with aqueous sodium hydroxide (4M) and water, dried ($MgSO_4$) and the solvent was evaporated under reduced pressure. The residue was dissolved in dichloromethane and washed with aqueous hydrochloric acid (2M), saturated aqueous sodium carbonate and water, dried ($MgSO_4$) and the solvent was evaporated under reduced pressure to give the title compound as a colorless oil (14 mg, 5%). δ7.58 (1H, s), 7.47 (2H, d, J 8.4 Hz), 7.39–7.16 (9H, m), 5.15 (2H, s), 4.22 (2H, s), 3.81 (2H, m), 3.61 (2H, m), 3.53 (3H, s), 3.15 (2H, m), and 3.00 (2H, m). m/z ($ES^+$) 564, 566 (M+1).

EXAMPLE 143

4-{3-[5-Chloro-2-(4-chlorophenyl)-1-methyl-1H-indol-3-yl]-1-oxopropyl}-1-(phenylmethyl)piperazinone Oxalyl chloride (0.08 mL, 114 mg, 0.9 mmol) was added dropwise to a stirred, cooled (0° C.) solution of 5-chloro-2-(4-chlorophenyl)-1-methyl-1H-indole-3-propanoic acid (Description 12, 330 mg, 0.95 mmol) and DMF (1 drop) in toluene (15 mL) and the mixture was stirred at room temperature for 2 h. to give a solution of 5-chloro-2-(4-chlorophenyl)-1-methyl-1H-indole-3-propanoyl chloride. A sample (7.5 mL) was added to a solution of 1-(phenylmethyl)piperazinone (*Tet.Lett.* 1996, 37, 7339–7342) (90 mg, 0.48 mmol) and triethylamine (0.1 mL, 73 mg, 0.72 mmol) in THF (5 mL) and the mixture was stirred at room temperature. Water was added and the mixture was extracted with ethyl acetate. The combined organic fractions were dried ($MgSO_4$) and the solvent was evaporated under reduced pressure. The residue was purified by flash column chromatography on silica gel, eluting with hexane/EtOAc (80:20) to give the title compound as a colorless foam. $^1$H NMR (360 MHz, $CDCl_3$) mixture of two amide rotamers; major isomer, δ7.57–7.18 (12H, m), 4.38 (2H, s), 3.86 (2H, s), 3.63 (2H, t, J 5.3 Hz), 3.55 (3H, s), 3.08–2.96 (4H, m), and 2.43 (2H, t, J 7.4 Hz); minor isomer, δ7.57–7.18 (12H, m), 4.57 (2H, s), 4.26 (2H, s), 3.50 (3H, s), 3.37 (2H, t, J 5.3 Hz), 3.08–2.96 (4H, m), and 2.48 (2H, t, J 7.4 Hz). m/z ($ES^+$) 520, 522 (M+1).

EXAMPLE 144

1-{3-[5-Chloro-2-(4-chlorophenyl)-1-methyl-1H-indol-3-yl]-1-thiopropyl}-4-(phenylmethyl)piperazine 2,4-Bis(4-methoxyphenyl)-1,3-dithia-2,4-diphosphetane-2,4-disulfide (2.5 mg, 6 μmol) was added to a solution of 1-{3-[5-chloro-2-(4-chlorophenyl)-1-methyl-1H-indol-3-yl]-1-oxopropyl}-4-(phenylmethyl)piperazine (Example 79, 6.0 mg, 12 μmol) in dioxane (3 mL) and the mixture was heated under reflux for 1 h. The mixture was cooled, water was added and the mixture was extracted with ethyl acetate. The combined organic fractions were dried (MgSO$_4$) and the solvent was evaporated under reduced pressure. The residue was purified by preparative TLC on silica gel, eluting with CH$_2$Cl$_2$/MeOH (98:2) to give the title compound (2 mg, 33%). $^1$H NMR (360 MHz, CDCl$_3$) δ7.64 (1H, s), 7.47 (2H, d, J 8.3 Hz), 7.32–7.23 (9H, m), 4.27 (2H, m), 3.54 (3H, s), 3.45 (2H, s), 3.38 (2H, m), 3.08 (2H, m), 3.00 (2H, m), 2.45 (2H, m), and 2.11 (2H, m). m/z (ES$^+$) 522, 524 (M+1).

EXAMPLE 145

-{3-[5-Chloro-2-(4-chlorophenyl)-1-methyl-1H-indol-3-yl]-1-oxopropyl}-4-(2,2-dimethylpropyl) piperazine Sodium triacetoxyborohydride (127 mg, 0.6 mmol) was added to a mixture of 1-{3-[5-chloro-2-(4-chlorophenyl)-1-methyl-1H-indol-3-yl]-1-oxopropyl}piperazine (Description 31, 50 mg, 0.12 mmol), 2,2-dimethylpropanal (16 μL, 12 mg, 0.14 mmol) and acetic acid (34 μL, 36 mg, 0.6 mmol) in 1,2-dichloroethane (5 mL) and the mixture was stirred at room temperature for 18 h. Saturated aqueous sodium hydrogen carbonate (20 mL) was added and the mixture was extracted with ethyl acetate (2×20 mL). The combined organic fractions were washed with brine (20 mL), dried (MgSO$_4$) and the solvent was evaporated under reduced pressure. The residue was purified by column chromatography on silica gel, eluting with hexane/EtOAc (80:20), to give the title compound as a brown foam (37 mg, 63%). $^1$H NMR (360 MHz, CDCl$_3$) δ7.58 (1H, d, J 1.8 Hz), 7.47 (2H, d, J 6.5 Hz), 7.31 (2H, d, J 6.5 Hz), 7.24 (1H, d, J 8.6 Hz), 7.22 (1H, dd, J 8.6, 1.8 Hz), 3.54 (3H, s), 3.53 (2H, m), 3.19 (2H, m), 2.98 (2H, m), 2.48 (2H, m), 2.41 (2H, m), 2.28 (2H, m), 2.01 (2H, s), and 0.85 (9H, s). m/z (ES$^+$) 486, 488 (M+1).

EXAMPLE 146

1-{3-[5-Chloro-2-(4-chlorophenyl)-1-methyl-1H-indol-3-yl]-1-oxopropyl}-4-(3,3-dimethylbutyl) piperazine Prepared from 1-{3-[5-chloro-2-(4-chlorophenyl)-1-methyl-1H-indol-3-yl]-1-oxopropyl}piperazine (Description 31) and 3,3-dimethylbutanal according to the method of Example 145. $^1$NMR (360 MHz, CDCl$_3$) δ7.58 (1H, d, J 1.7 Hz), 7.48 (2H, d, J 6.5 Hz), 7.31 (2H, d, J 6.5 Hz), 7.24 (1H, d, J 8.6 Hz), 7.20 (1H, dd, J 8.6, 1.7 Hz), 3.58 (2H, m), 3.54 (3H, s), 3.23 (2H, m), 2.98 (2H, m), 2.50 (2H, m), 2.33 (2H, m), 2.28 (2H, m), 2.20 (2H, m), 1.37 (2H, m), and 0.90 (9H, s). m/z (ES$^+$) 500, 502 (M+1).

EXAMPLE 147

(3S)-1-{3-[5-Chloro-2-(4-chlorophenyl)-1-methyl-1H-indol-3-yl]-1-oxopropyl}-4-methyl-3-(phenylmethyl)piperazine Prepared from 5-chloro-2-(4-chlorophenyl)-1-methyl-1H-indole-3-propanoic acid (Description 12) and (2S)-1-methyl-2-(phenylmethyl)piperazine (Description 35) according to the method of Description 25. $^1$H NMR (400 MHz, CDCl$_3$) mixture of two amide rotamers; δ7.56–6.98 (12H, m), 4.09, 3.93 (total 1H, each d, J 13.1 Hz), 3.53, 3.47 (total 3H, each s), 3.20–1.98 (12H, m), and 2.39, 2.38 (total 3H, each s). m/z (ES$^+$) 520, 522 (M+1).

EXAMPLE 148

1-{3-[2-(5-Chloro-4-chlorophenyl)-1-(methylsulfonyl)-1H-indol-3-yl]-1-oxopropyl}-4-(2-methoxyphenyl)piperazine Sodium hydride (60% dispersion in mineral oil, 13 mg, 0.3 mmol) was added to a solution of 1-{3-[2-(5-chloro-4-chlorophenyl)-1H-indol-3-yl]-1-oxopropyl}-4-(2-methoxyphenyl)piperazine (Example 85, 52 mg, 0.1 mmol) in N,N-dimethylformamide (1 mn) and the mixture was stirred at room temperature for 5 min. Methanesulfonyl chloride (10 μl, 15 mg, 0.13 mmol) was added and the mixture was stirred at room temperature for 10 min. Further sodium hydride (60% dispersion in mineral oil, 50 mg, 1.2 mmol) and methanesulfonyl chloride (20 μl, 30 mg, 0.26 mmol) were added and the mixture was stirred at room temperature for 10 min. Saturated aqueous ammonium chloride (10 mL) was added and the mixture was extracted with ethyl acetate. The combined organic fractions were washed with aqueous ammonium chloride (10%, 10 mL) dried (Na$_2$SO$_4$) and the solvent was evaporated under reduced pressure. The residue was purified by flash column chromatography on silica gel, eluting with hexane/ether (50:50) to give the title compound as a colorless glass (30 mg, 51%). $^1$H NMR (360 MHz, CDCl$_3$) δ8.04 (1H, d, J 8.8 Hz), 7.62 (1H, d, J 2.1 Hz), 7.45 (2H, d, J 8.5 Hz), 7.37 (2H, d, J 8.5 Hz), 7.36 (1H, dd, J 8.8, 2.1 Hz), 7.03 (1H, t, J 7.7 Hz), 6.94–6.85 (3H, m), 3.87 (3H, s), 3.75 (2H, m), 3.38 (2H, m), 2.98–2.86 (6H, m), 2.81 (3H, s), and 2.45 (2H, m). m/z (ES$^+$) 586, 588 (M+1).

What is claimed is:

1. A compound of the formula (I):

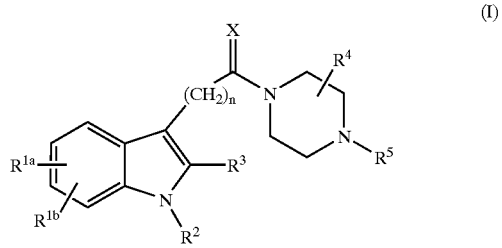

wherein
R$^{1a}$ and R$^{1b}$ each independently represent hydrogen, C$_{1-6}$alkyl, C$_{1-6}$alkoxy, fluoroC$_{1-6}$alkyl, fluoroC$_{1-6}$alkoxy, halogen, cyano, NR$^a$R$^b$, SR$^a$, SOR$^a$, SO$_2$R$^a$, OSO$_2$R$^a$, NR$^a$COR$^b$, COR$^a$, CO$_2$R$^a$ or CONR$^a$R$^b$;

R$^2$ represents hydrogen, C$_{1-6}$alkyl, fluoroC$_{1-6}$alkyl, (CH$_2$)$_m$COR$^a$, (CH$_2$)$_p$CO$_2$R$^a$, (CH$_2$)$_p$OH, (CH$_2$)$_m$CONR$^a$R$^b$, (CH$_2$)$_m$phenyl or SO$_2$C$_{1-6}$alkyl;

R$^3$ represents phenyl, biphenyl or naphthyl, wherein said phenyl group is optionally substituted by one, or two groups independently selected from halogen, C$_{1-6}$alkyl, C$_{1-6}$alkoxy, trifluoroC$_{1-6}$alkyl, fluoroC$_{1-6}$alkoxy, or C$_{2-6}$alkenyl;

R$^4$ represents hydrogen, methyl, carbonyl, benzyl or a methylene bridge across the 2,5-positions on the piperazine ring;

R$^5$ represents C$_{3-6}$alkyl, C$_{5-7}$cycloalkyl, C$_{3-7}$cycloalkylC$_{1-2}$alkyl, C$_{2-4}$alkenyl, phenyl naphthyl, fluorenyl, heteroaryl (wherein heteroaryl is selected from the group consisting of pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl), CH$_2$phenyl, (CH$_2$)$_2$phenyl, CH$_2$heteroaryl (wherein heteroaryl is as defined above), CH(phenyl)$_2$, CH(C$_{1-2}$alkyl)(phenyl), C$_{2-4}$alkenyl(phenyl), CH$_2$N(C$_{2-4}$alkenyl)$_2$, CH$_2$CONR$^c$R$^d$, COphenyl or (CH$_2$)$_m$CO$_2$R$^c$ (wherein R$^c$ represents hydrogen or C$_{1-4}$alkyl and m is zero or 1), and wherein said phenyl or heteroaryl groups are optionally substituted by one or two groups independently selected from halogen, $C_{1-4}$alkyl, $C_{1-4}$alkoxy, fluoro$C_{1-4}$alkyl, fluoro$C_{1-4}$alkoxy, $NO_2$, cyano and S($C_{1-4}$alkyl) or said phenyl or heteroaryl groups are optionally substituted by the group —$(CH_2)_{1-2}O$—;

$R^a$ and $R^b$ each independently represent hydrogen, $C_{1-4}$alkyl or fluoro$C_{1-4}$alkyl;

$R^c$ and $R^d$ each independently represent hydrogen, $C_{1-4}$alkyl, $C_{2-4}$alkenyl, phenyl or benzyl or $R^c$ and $R^d$, together with the nitrogen atom to which they are attached, form pyrrolidine or piperidine to which there is fused a benzene ring;

X represents an oxygen atom;

m is zero or an integer from 1 to 4;

n is an integer selected from 2, 3 and 4;

p is an integer from 1 to 4;

or a pharmaceutically acceptable salt thereof.

2. A compound as claimed in claim 1 wherein $R^{1a}$ and $R^{1b}$ each independently represent hydrogen, $C_{1-6}$alkyl, fluoro$C_{1-6}$alkoxy or halogen.

3. A compound as claimed in claim 1 wherein $R^2$ represents hydrogen, $C_{1-6}$alkyl, fluoro$C_{1-6}$alkyl, $(CH_2)_mCOR^a$, $(CH_2)_pCO_2R^a$, $(CH_2)_pOH$ or $(CH_2)_m$phenyl.

4. A compound of the formula (Ia)

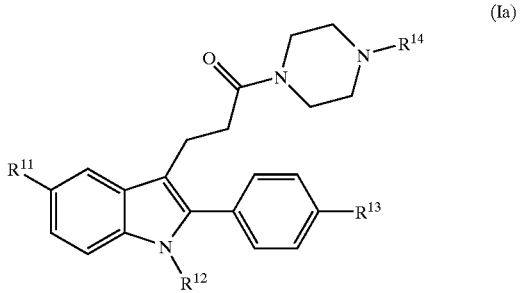

(Ia)

or a pharmaceutically acceptable salt thereof, wherein:

$R^{11}$ represents a chlorine atom or a methyl group;

$R^{12}$ represents a hydrogen atom or a group selected from $C_{1-3}$alkyl, fluoro$C_{1-3}$alkyl, $COCH_3$, or $(CH_2)_2OH$;

$R^{13}$ represents a halogen atom or a group selected from $C_{1-4}$alkyl, $C_{2-4}$alkenyl, fluoro$C_{1-4}$alkyl, $C_{1-4}$alkoxy or fluoro$C_{1-4}$alkoxy; and $R^{14}$ represents a group selected from $C_{3-6}$alkyl, $C_{5-7}$cyctoalkyl, $C_{3-7}$cycloalkyl$C_{1-2}$alkyl, phenyl, naphthyl, benzyl, α-methylbenzyl, phenylethyl, —$CH_2CON(CH_3)$phenyl, —$CH_2CON(CH_3)$benzyl, —$CH_2CONR^cR^d$ (where $R^c$ and $R^d$, together with the nitrogen atom to which they are attached, form a pyrrolidine or piperidine ring, to which ring there is fused a benzene ring), —$CH_2CON(CH_3)C_{2-4}$alkenyl, or —$(CH_2)_mCO_2R^c$ (where $R^c$ is hydrogen or $C_{1-4}$alkyl and m is zero or 1), wherein said phenyl and benzyl groups may be substituted by a group selected from halogen, $C_{1-3}$alkyl, $C_{1-3}$alkoxy, fluoro$C_{1-3}$alkyl, fluoro$C_{1-3}$alkoxy, $NO_2$, cyano, and —S—$C_{1-3}$alkyl or said phenyl and benzyl groups may be substituted by the group —O—$CH_2$—O—.

5. A pharmaceutical composition comprising a compound as claimed in claim 1, together with at least one pharmaceutically acceptable carrier or excipient.

6. A method for the treatment or prevention of pain, inflammation, migraine, emesis, postherpetic neuralgia, depression or anxiety, which method comprises administration to a patient in need thereof of an effective amount of the compound of claim 1.

* * * * *